United States Patent
Hagen

(10) Patent No.: US 7,611,721 B1
(45) Date of Patent: Nov. 3, 2009

(54) ADJUVANT COMBINATION FORMULATIONS

(75) Inventor: Michael Hagen, Pittsford, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/009,473

(22) PCT Filed: May 12, 2000

(86) PCT No.: PCT/US00/13156

§ 371 (c)(1),
(2), (4) Date: Nov. 8, 2001

(87) PCT Pub. No.: WO00/69456

PCT Pub. Date: Nov. 23, 2000

(51) Int. Cl.
*A61K 47/00* (2006.01)
(52) U.S. Cl. .................................... 424/278.1
(58) Field of Classification Search ............ 435/5, 435/235.1; 424/1.11, 1.17, 1.41, 278.1, 281.1, 424/282.1; 514/885
See application file for complete search history.

(56) References Cited

U.S. PATENT DOCUMENTS

| | | | |
|---|---|---|---|
| 4,666,829 A | 5/1987 | Glenner et al. | |
| 4,912,094 A | 3/1990 | Myers et al. | |
| 5,013,548 A | 5/1991 | Haynes et al. | |
| 5,019,387 A | 5/1991 | Haynes et al. | |
| 5,057,540 A | 10/1991 | Kensil | |
| 5,073,627 A | 12/1991 | Curtis et al. | |
| 5,078,996 A | 1/1992 | Conlon, III et al. | |
| 5,223,254 A | 6/1993 | Paradiso et al. | |
| 5,229,496 A | 7/1993 | Deeley et al. | |
| 5,571,515 A | 11/1996 | Scott et al. | |
| 5,593,972 A | 1/1997 | Weiner et al. | |
| 5,603,958 A * | 2/1997 | Morein et al. ............... 424/489 |
| 5,679,356 A | 10/1997 | Bonnem et al. | |
| 5,723,127 A | 3/1998 | Scott et al. | |
| 5,723,130 A | 3/1998 | Hancock et al. | |
| 5,736,361 A | 4/1998 | Carbonetti et al. | |
| 5,762,943 A | 6/1998 | Dolovich et al. | |
| 5,776,468 A | 7/1998 | Hauser et al. | |
| 5,830,877 A | 11/1998 | Carson et al. | |
| 5,861,243 A | 1/1999 | Dietrich et al. | |
| 5,932,216 A | 8/1999 | Celeste et al. | |
| 5,939,074 A | 8/1999 | Berzofsky | |
| 5,955,087 A * | 9/1999 | Whittle et al. ........... 424/204.1 |
| 5,976,539 A | 11/1999 | Scott et al. | |
| 5,980,911 A | 11/1999 | Corner et al. | |
| 5,993,819 A * | 11/1999 | Haynes et al. ........... 424/188.1 |
| 6,024,965 A | 2/2000 | van Baalen et al. | |
| 6,037,135 A | 3/2000 | Kubo et al. | |
| 6,071,893 A | 6/2000 | Graham et al. | |
| 6,096,313 A | 8/2000 | Jager et al. | |
| 6,113,918 A | 9/2000 | Johnson et al. | |
| 6,350,456 B1 * | 2/2002 | Reed et al. ............... 424/248.1 |
| 6,488,936 B1 | 12/2002 | Mishkin et al. | |
| 6,514,503 B1 | 2/2003 | Gizurarson et al. | |
| 6,613,337 B1 | 9/2003 | Reed et al. | |
| 6,797,276 B1 * | 9/2004 | Glenn et al. ............. 424/278.1 |
| 6,929,794 B1 | 8/2005 | Mills et al. | |

FOREIGN PATENT DOCUMENTS

| | | |
|---|---|---|
| EP | 671947 | 3/2000 |
| WO | WO 90/05147 | 5/1990 |
| WO | WO 91/16819 | 11/1991 |
| WO | WO 95/29700 | 11/1995 |
| WO | WO 96/10423 | 4/1996 |
| WO | WO 96/11019 | 4/1996 |
| WO | WO 97/28273 | 8/1997 |
| WO | WO 98/17799 | 4/1998 |
| WO | WO 98/20734 | 5/1998 |
| WO | WO 98/50399 | 11/1998 |
| WO | WO 98/56415 | 12/1998 |
| WO | WO 98/57659 | 12/1998 |
| WO | WO 9857659 | * 12/1998 |
| WO | WO 99/02132 | 1/1999 |
| WO | WO 99/12565 | 3/1999 |
| WO | WO 99/27944 | 6/1999 |
| WO | WO 99/40937 | 8/1999 |
| WO | WO 99/51259 | 10/1999 |
| WO | WO 00/60084 | 10/2000 |
| WO | WO 00/69456 | 11/2000 |

OTHER PUBLICATIONS

Result No. 1 of RAG Sequence Result Summary.*
Ulrich et al. Monophosphoryl lipid A as an adjuvant. Past experiences and new directions. In M.F. Powell and M.J. Newman (ed.), Vaccine Design. Plenum Press, New York, NY, p. 495-524.*
Disis et al. Granulocyte-macrophage colony-stimulating factor: an effective adjuvant for protein and peptide based vaccines. Blood, 1996; vol. 88, No. 1: 202-210.*
Bartlett et al. Safety and immunogenicity of an HLA-based HIV envelope polyvalent synthetic peptide immunogen. AIDS, 1998, vol. 12, No. 11, 1291-1300.*
Finkelman, F.D. and Holmes, J., Ann Rev Immunol 8:303-333 (1990).
Snapper, C.M. et al., J Exp Med 175:1367-1371 (1992).
Kobayashi, M., et al., J Exp Med 170:827-845 (1989).
Alderson, M.R. et al., J Exp Med 178:669-674 (1993).
Snapper, C.M. et al., J Immunol 154:5842-5850 (1995).
Charbit, A. et al., Vaccine 11:1221-1228 (1993).
Natuk, R.J. et al., AIDS Res Hum Retroviruses 9:395-404 (1993).
Johnson, R.P. et al., J Virol 68:3145-3153 (1994).
Fuller, D.H. et al., AIDS Res Hum Retroviruses 10:1433-1441 (1994).

(Continued)

*Primary Examiner*—Emily M. Le
(74) *Attorney, Agent, or Firm*—Kelly M. Sullivan; Alan M. Gordon

(57) ABSTRACT

The use of 3-O-deacylated monophosphoryl lipid A or monophosphoryl lipid A and derivatives and analogs thereof, in combination with a cytokine or lymphokine such as granulocyte macrophage colony stimulating factor or interleukin-12 is useful as an adjuvant combination in an antigenic composition to enhance the immune response in a vertebrate host to a selected antigen.

55 Claims, 5 Drawing Sheets

OTHER PUBLICATIONS

Berzofsky, J.A. et al., J Clin Invest 88:876-884 (1991).
Palker, T.J. et al., J Immunol 142:3612-3619 (1989).
Hart, M.K. et al., J Immunol 145:2677-2685 (1990).
Haynes, B.F. et al., J Immunol 151:1646-1653 (1993).
Hart, M.K. et al., Proc Natl Acad Sci USA 88:9448-9452 (1991).
Bartlett, J.A. et al., AIDS 12:1291-1300 (1998).
Haynes, B.F. et al., AIDS Res Hum Retroviruses 11:211-221 (1998).
Staats, H.F. et al., J Immunol 157:462-472 (1996).
Porgador, A. et al., J Immunol 158:834-841 (1997).
Allen, T.M. et al., J Immunol 160:6062-6071 (1998).
Miller, M.D. et al., J Immunol 147:320-329 (1991).
Egan, M.A. et al., J Virol 73:5466-5472 (1999).
Kuroda, M.J. et al., J Exp Med 187:1373-1381 (1998).
Shijns, Virgil EJC; Immunological concepts of vaccine adjuvant activity; Commentary; Current Opinion in Immunology; 2000, 12:456-463.
Abbas, Abul K., et al.; Cellular And Molecular Immunology; Cytokines; Library of Congress Cataloging-in-Publication Data; 1994; Chapter 12; pp. 240-260.
Vaslin, B. et al., Vaccine 12:1132-1140 (1994).
Mosmann, T.R. et al., J Immunol 136:2348-2357 (1986).
Ahlers, J.D. et al., J Immunol 158:3947-3958 (1997).
Scharton-Kersten, T. et al., J Immunol 154:5320-5330 (1995).
Ghalib, H.W. et al., J Immunol 154:4623-4629 (1995).
Murray, H.W. and Hariprashad, J., J Exp Med 181:387-391(1995).

USPTO Final Office Action, Mailed Mar. 17, 2008, Hagen, Michael, U.S. Appl. No. 10/416,262, filed May 8, 2003, Adjuvant Combination Formulations.
USPTO Final Office Action, Mailed Oct. 17, 2008, Hagen, Michael, U.S. Appl. No. 11/544,056, filed Oct. 6, 2006, Adjuvant Combination Formulations.
Silla, S. et al., "Enhancement by IL-12 of the cytolytic T lymphocyte (CTL) response of mice immunized with tumor-specific peptides in an adjuvant containing QS21 and MPL," 1999, European Cytokine Network, vol. 10(2), pp. 181-189.
Hancock, G. E. et al., "QS-21 Synergizes with Recombinant Interleukin-12 to Create a Potent Adjuvant Formulation for the Fusion Protein of Respiratory Syncytial Virus," 2000, Viral Immunology, vol. 13(4), pp. 503-509.
Weinberg, A. et al., "Recombinant Interleukin 2 As An Adjuvant for Vaccine-induced Protection," Jan. 1, 1988, Journal of Immunology, vol. 140(1), pp. 294-299.
Datta, S. K. et al, "Antigen-immunostimulatory oligo-nucleotide conjugates: mechanisms and applications," Jun. 2004, Immunological Reviews, vol. 199, pp. 217-226, Abstract Only.
Schoenhaut, D. S. et al., "Cloning and Expression of Murine IL-12," Jun. 1, 1992, Journal of Immunology, vol. 148(11), pp. 3433-3440.
Singh, M. et al., "Advances in vaccine adjuvants," Nov. 1999, Nature Biotechnology, vol. 17(11), pp. 1075-1081.
Vaslin, B. et al., "Induction of humoral and cellular immunity to simian immunodeficiency virus: what are the requirements for protection?" 1994, Vaccine, vol. 12, pp. 1132-1140.

\* cited by examiner

SEQUENCE LISTING

<160> NUMBER OF SEQ ID NOS: 14

<210> SEQ ID NO 1
<211> LENGTH: 40
<212> TYPE: PRT
<213> ORGANISM: Human immunodeficiency virus

<400> SEQUENCE: 1

Lys Gln Ile Ile Asn Met Trp Gln Glu Val Gly Lys Ala Met Tyr Ala
 1               5                  10                  15

Cys Thr Arg Pro Asn Tyr Asn Lys Arg Lys Arg Ile His Ile Gly Pro
            20                  25                  30

Gly Arg Ala Phe Tyr Thr Thr Lys
        35                  40

<210> SEQ ID NO 2
<211> LENGTH: 39
<212> TYPE: PRT
<213> ORGANISM: Human immunodeficiency virus

<400> SEQUENCE: 2

Lys Gln Ile Ile Asn Met Trp Gln Glu Val Gly Lys Ala Met Tyr Ala
 1               5                  10                  15

Thr Arg Pro Asn Tyr Asn Lys Arg Lys Arg Ile His Ile Gly Pro Gly
            20                  25                  30

Arg Ala Phe Tyr Thr Thr Lys
        35

<210> SEQ ID NO 3
<211> LENGTH: 9
<212> TYPE: PRT
<213> ORGANISM: Simian immunodeficiency virus

<400> SEQUENCE: 3

Cys Thr Pro Tyr Asp Ile Asn Gln Met
 1               5

<210> SEQ ID NO 4
<211> LENGTH: 9
<212> TYPE: PRT
<213> ORGANISM: Simian immunodeficiency virus

<400> SEQUENCE: 4

Ser Thr Pro Pro Leu Val Arg Leu Val
 1               5

```
<210> SEQ ID NO 5
<211> LENGTH: 9
<212> TYPE: PRT
<213> ORGANISM: Simian immunodeficiency virus

<400> SEQUENCE: 5

Tyr Ala Pro Pro Ile Ser Gly Gln Ile
 1               5

<210> SEQ ID NO 6
<211> LENGTH: 20
<212> TYPE: PRT
<213> ORGANISM: Simian immunodeficiency virus

<400> SEQUENCE: 6

Glu Leu Tyr Lys Tyr Lys Val Val Lys Ile Glu Pro Leu Gly Val Ala
 1               5                  10                  15

Pro Thr Lys Ala
            20

<210> SEQ ID NO 7
<211> LENGTH: 29
<212> TYPE: PRT
<213> ORGANISM: Simian immunodeficiency virus

<400> SEQUENCE: 7

Glu Leu Tyr Lys Tyr Lys Val Val Lys Ile Glu Pro Leu Gly Val Ala
 1               5                  10                  15

Pro Thr Lys Ala Cys Thr Pro Tyr Asp Ile Asn Gln Met
            20                  25

<210> SEQ ID NO 8
<211> LENGTH: 29
<212> TYPE: PRT
<213> ORGANISM: Simian immunodeficiency virus

<400> SEQUENCE: 8

Glu Leu Tyr Lys Tyr Lys Val Val Lys Ile Glu Pro Leu Gly Val Ala
 1               5                  10                  15

Pro Thr Lys Ala Ser Thr Pro Pro Leu Val Arg Leu Val
            20                  25

<210> SEQ ID NO 9
<211> LENGTH: 29
<212> TYPE: PRT
<213> ORGANISM: Simian immunodeficiency virus

<400> SEQUENCE: 9

Glu Leu Tyr Lys Tyr Lys Val Val Lys Ile Glu Pro Leu Gly Val Ala
 1               5                  10                  15

Pro Thr Lys Ala Tyr Ala Pro Pro Ile Ser Gly Gln Ile
            20                  25

<210> SEQ ID NO 10
<211> LENGTH: 42
<212> TYPE: PRT
<213> ORGANISM: Unknown Organism
<220> FEATURE:
<223> OTHER INFORMATION: Description of Unknown Organism: Human amyloid
      peptide protein

<400> SEQUENCE: 10
```

-continued

```
Asp Ala Glu Phe Arg His Asp Ser Gly Tyr Glu Val His His Gln Lys
  1               5                  10                  15

Leu Val Phe Phe Ala Glu Asp Val Gly Ser Asn Lys Gly Ala Ile Ile
             20                  25                  30

Gly Leu Met Val Gly Val Val Ile Ala
         35                  40

<210> SEQ ID NO 11
<211> LENGTH: 28
<212> TYPE: PRT
<213> ORGANISM: Unknown Organism
<220> FEATURE:
<223> OTHER INFORMATION: Description of Unknown Organism: Human amyloid
      peptide protein

<400> SEQUENCE: 11

Asp Ala Glu Phe Arg His Asp Ser Gly Tyr Glu Val His His Gln Lys
  1               5                  10                  15

Leu Val Phe Phe Ala Glu Asp Val Gly Ser Asn Lys
             20                  25

<210> SEQ ID NO 12
<211> LENGTH: 10
<212> TYPE: PRT
<213> ORGANISM: Human immunodeficiency virus

<400> SEQUENCE: 12

Arg Gly Pro Gly Arg Ala Phe Val Thr Ile
  1               5                  10

<210> SEQ ID NO 13
<211> LENGTH: 10
<212> TYPE: PRT
<213> ORGANISM: Human immunodeficiency virus

<400> SEQUENCE: 13

Ile Gly Pro Gly Arg Ala Phe Tyr Thr Thr
  1               5                  10

<210> SEQ ID NO 14
<211> LENGTH: 9
<212> TYPE: PRT
<213> ORGANISM: Influenza virus

<400> SEQUENCE: 14

Thr Tyr Gln Arg Thr Arg Ala Leu Val
  1               5
```

ADJUVANT COMBINATION FORMULATIONS

FIELD OF THE INVENTION

This invention relates to the use of 3-O-deacylated monophosphoryl lipid A or monophosphoryl lipid A and derivatives and analogs thereof, in combination with a cytokine or lymphokine, in particular granulocyte macrophage colony stimulating factor or interleukin-12, as an adjuvant formulation in an antigenic composition to enhance the immune response in a vertebrate host to a selected antigen.

BACKGROUND OF THE INVENTION

The immune system uses a variety of mechanisms for attacking pathogens. However, not all of these mechanisms are necessarily activated after immunization. Protective immunity induced by immunization is dependent on the capacity of the vaccine to elicit the appropriate immune response to resist or eliminate the pathogen. Depending on the pathogen, this may require a cell-mediated and/or humoral immune response.

The current paradigm for the role of helper T cells in the immune response is that T cells can be separated into subsets on the basis of the cytokines they produce, and that the distinct cytokine profile observed in these cells determines their function. This T cell model includes two major subsets: TH-1 cells that produce interleukin-2 (IL-2) and interferon gamma, which augment both cellular and humoral (antibody) immune responses; and TH-2 cells that produce interleukin-4, interleukin-5 and interleukin-10 (IL-4, IL-5 and IL-10, respectively), which augment humoral immune responses (Bibliography entry 1).

It is often desirable to enhance the immunogenic potency of an antigen in order to obtain a stronger immune response in the organism being immunized and to strengthen host resistance to the antigen-bearing agent. In some situations, it is desirable to shift the immune response from a predominantly humoral (TH-2) response to a more balanced cellular (TH-1) and humoral (TH-2) response.

A cellular response involves the generation of a CD8+ CTL (cytotoxic T-lymphocyte) response. Such a response is desirable for the development of vaccines against intracellular pathogens. Protection against a variety of pathogens requires strong mucosal responses, high serum titers, induction of CTL and vigorous cellular responses. These responses have not been provided by most antigen preparations, including conventional subunit vaccines. Among such pathogens is the human immunodeficiency virus (HIV).

Thus, there is a need to develop antigenic composition formulations that are able to generate both humoral and cellular immune responses in a vertebrate host.

SUMMARY OF THE INVENTION

Accordingly, it is an object of this invention to utilize adjuvant combination formulations in antigenic compositions containing 3-O-deacylated monophosphoryl lipid A (MPL™) or monophosphoryl lipid A and derivatives and analogs thereof, combined with a cytokin or lymphokine, in particular granulocyte-macrophage colony stimulating factor (GM-CSF) or interleukin-12 (IL-12), or an agonist or antagonist to said cytokine or lymphokine. An adjuvant is a substance that enhances the immune response when administered together with an immunogen or antigen. The adjuvant formulation of this invention is administered together with a selected antigen in an antigenic composition. The antigenic compositions of this invention enhance the immune response in a vertebrate host to that selected antigen. The selected antigen may be a polypeptide, peptide or fragment derived (1) from a pathogenic virus, bacterium, fungus or parasite, or (2) from a cancer cell or tumor cell, or (3) from an allergen so as to interfere with the production of IgE so as to moderate allergic responses to the allergen, or (4) from Aβ protein or peptide thereof so as to prevent or treat disease characterized by amyloid deposition in a vertebrate host. In one embodiment of the invention, the selected antigen is from HIV. The selected HIV antigen may be an HIV protein, polypeptide, peptide or fragment derived from said protein. In a particular embodiment of the invention, the HIV antigen is a specific peptide. In other embodiments of the invention, the selected antigen is from *Neisseria gonorrhoeae* or Respiratory syncytial virus.

The MPL™ can be present as an aqueous solution, or as a stabilized oil-in-water emulsion (stable emulsion or SE). In a preferred embodiment of the invention, the oil-in-water emulsion contains squalene, glycerol and phosphatidyl choline. In the SE formulation, the MPL™ is mixed with the cytokine or lymphokine to form the antigenic composition prior to administration. The cytokine or lymphokine is not required to enter the emulsion. In a preferred embodiment of the invention, the MPL™ is in the SE form. The antigenic composition may further comprise a diluent or carrier.

The invention is also directed to methods for increasing the ability of an antigenic composition containing a selected antigen (1) from a pathogenic virus, bacterium, fungus or parasite to elicit the immune response of a vertebrate host, or (2) from a cancer antigen or tumor-associated antigen from a cancer cell or tumor cell to elicit a therapeutic or prophylactic anti-cancer effect in a vertebrate host, or (3) from an allergen so as to interfere with the production of IgE so as to moderate allergic responses to the allergen, or (4) from Aβ protein or peptide thereof so as to prevent or treat disease characterized by amyloid deposition in a vertebrate host, by including an effective adjuvanting amount of a combination of a cytokine or lymphokine, in particular MPL™ with GM-CSF or IL-12, or an agonist or antagonist to said cytokine or lymphokine.

The invention is further directed to methods for increasing the ability of an antigenic composition containing a selected antigen from a pathogenic virus, bacterium, fungus or parasite to elicit cytotoxic T lymphocytes in a vertebrate host by including an effective adjuvanting amount of a combination of a cytokine or lymphokine, in particular MPL™ with GM-CSF or IL-12, or an agonist or antagonist to said cytokine or lymphokine.

μg/dose. MPL™ was delivered to mice at a final concentration of 50 μg as an aqueous formulation, or at 25 μg as part of a stable emulsion with 1% SE. Titers were determined two weeks after the second immunization. The data represent individual titers determined from five mice.

Figure 3:
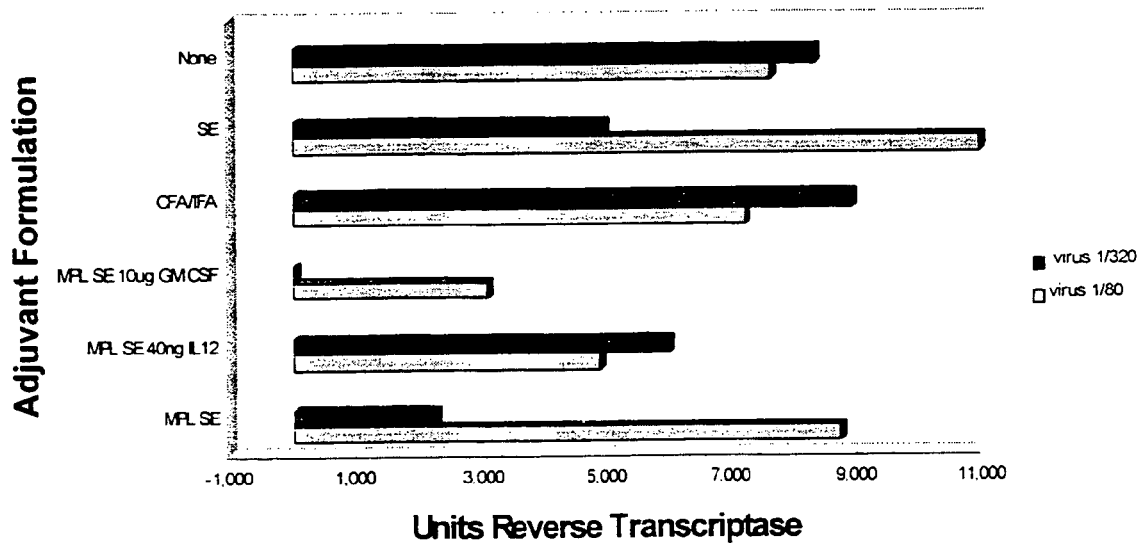

FIG. 3 depicts the results of a viral neutralization assay. Pooled sera taken at day 42 from mice immunized at days 0 and 28 with the indicated formulations were diluted (1/1600) and added to dilutions of T cell-adapted $HIV_{MN}$ prior to addition to AA5 cells in vitro. After seven days culture, the cell culture supernatants were assayed for viral reverse transcriptase as an indicator of viral replication.

Figure 4:
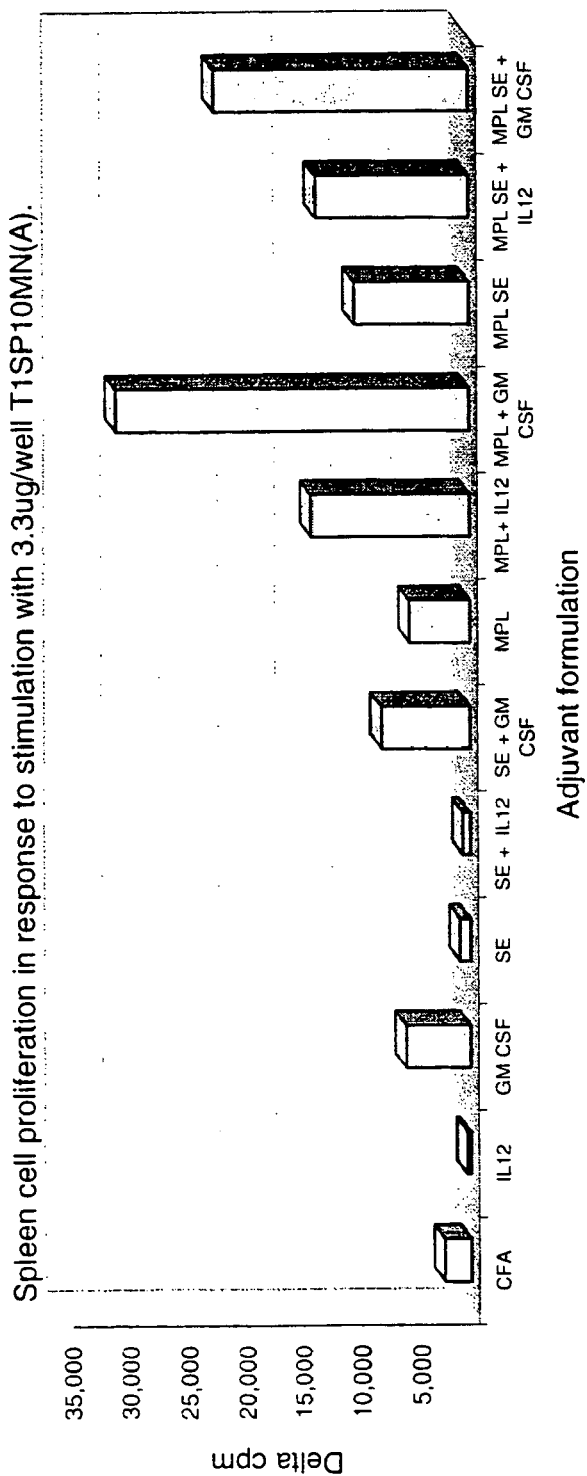

FIG. 4 depicts the proliferation of spleen cells from mice immunized with T1SP10MN(A) (-Cys) and various adjuvant formulations. Spleen cells were stimulated in vitro for four days with 3.3 μg/ml T1SP10MN(A) (-Cys). The results are shown as the change in the incorporation of label d thymidine as a result of in vitro stimulation with T1SP10MN(A) (-Cys) over the incorporation in the absence of stimulation (delta cpm).

Figure 5:
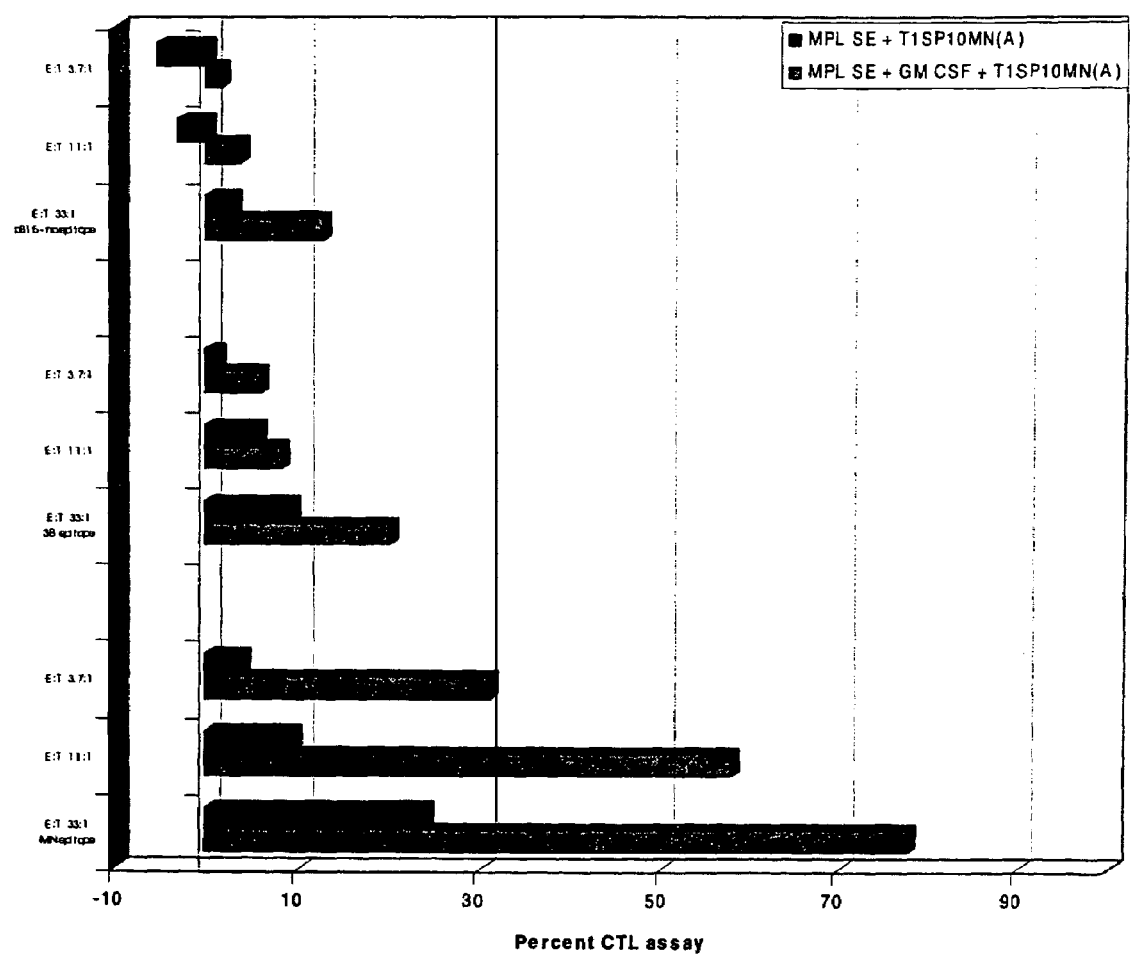

FIG. 5 depicts the CTL activity of spleen cells isolated from mice seven days after secondary immunization. Spleen cells were harvested from groups of three Balb/c mice immunized on days 0 and 21 with 50 μg T1SP10MN(A) (-Cys) formulated with 50 μg MPL™ in 1% SE with or without 10 μg GM-CSF. Cells were cultured with the $HIV_{MN}$ CTL epitope peptide for seven days. IL-2 was added to the cultures for the last five days. Effector spleen cells were added to chromium-labelled P815 cells pulsed with $HIV_{MN}$, another strain designated $HIV_{IIIB}$ or no peptide at the indicated ratios. Percent CTL activity was calculated as:

$$\frac{\text{specifically released } cpm - \text{spontaneously released } cpm}{\text{total maximum } cpm - \text{spontaneously released } cpm} \times 100$$

"E:T" means effector to target cell ratio.

DETAILED DESCRIPTION OF THE INVENTION

Adjuvants, cytokines and lymphokines are immune modulating compounds which have the ability to enhance and steer the development and profile of immune responses against various antigens that are themselves poorly immunogenic. The appropriate selection of adjuvants, cytokines and lymphokines can induce good humoral and cellular immune responses that would not develop in the absence of adjuvant, cytokine or lymphokine. In particular, adjuvants, cytokines and lymphokines have significant effects in enhancing the immune response to subunit and peptide antigens in vaccines. Their stimulatory activity is also beneficial to the development of antigen-specific immune responses directed against protein antigens. For a variety of antigens that require strong mucosal responses, high serum titers, induction of CTL and vigorous cellular responses, adjuvant and cytokine/lymphokine combinations provide stimuli that are not provided by most antigen preparations.

Numerous studies have evaluated different adjuvant formulations in animal models, but alum (aluminum hydroxide or aluminum phosphate) is currently the only adjuvant licensed for widespread use in humans. One group of adjuvants, stable emulsions, consisting of various water-in-oil or oil-in-water combinations, has received considerable attention for their immunopotentiating ability. These formulations generally consist of various combinations of metabolizable or inert oils, that act to stabilize and depot antigen at the site of injection. One such adjuvant is incomplete Freund's adjuvant (IFA), which includes mineral oil, water and an emulsifying agent. Complete Freund's adjuvant (CFA) is IFA plus heat-killed *Mycobacteria*. A particular concern in using these types of adjuvants has been injection site-associated irritation, often the result of mononuclear cell infiltrations causing granulomatous lesions. Therefore, other compounds and formulations are being investigated as potential adjuvants.

One such compound is 3-O-deacylated monophosphoryl lipid A (MPL™), which is available from Ribi ImmunoChem Research Inc. (Hamilton, Mont.). MPL™ is described in U.S. Pat. No. 4,912,094 (2), which is hereby incorporated by reference.

Recently, Ribi ImmunoChem Research Inc. has formulated a metabolizable oil-in-water formulation which, when combined with MPL™, results in the formation of a stabilized emulsion designated MPL™ SE. The stabilized emulsion is generated through microfluidization of MPL™ with squalene oil, glycerol and phosphatidyl choline. The current formulation is a GMP-quality microfluidized emulsion. Emulsions containing 1 or 2% oil are described in the experiments below.

MPL™ SE resulted in no discernable injection-site associated tissue pathology when administered subcutaneously, or intramuscularly into Balb/c mice. A stabilized emulsion containing the same components, but without MPL™, was also generated for comparative purposes. Specifically, subcutaneous or intramuscular immunization with a 40 amino acid HIV peptide T1SP10MN(A) (+Cys), or with a cysteine-deleted 39 amino acid peptide T1SP10MN(A) (-Cys) peptide (which lacks the cysteine residue at amino acid number 17 of the 40 amino acid peptide (+Cys)), formulated with the combination of adjuvants MPL™ SE and GM-CSF resulted in no discernable cellular infiltration or tissue abnormalities two weeks after immunization.

Also within the scope of this invention is the use of monophosphoryl lipid A, a precursor form of MPL™, which is also described in U.S. Pat. No. 4,912,094 (2). Further within the scope of this invention are derivatives and analogs of MPL™ and monophosphoryl lipid A.

The incorporation of cytokines and lymphokines into vaccine formulations has shown promise for the expansion and enhancement of vaccine potential (3). The cytokine interleukin-12 (IL-12) has been demonstrated to evoke and enhance cell mediated immunity, through a shift in T helper cell subset expansion towards a Th1 cytokine profile (i.e., to IgG2 subclass in the mouse model) (4-6). In mice, recombinant murine IL-12 has been shown to enhance a Th1 dominated immune response profile (3).

IL-12 is produced by a variety of antigen-presenting cells, principally macrophages and monocytes. It is a critical element in the induction of TH1 cells from naïve T-cells. Production of IL-12 or the ability to respond to it has been shown to be critical in the development of protective TH1-like responses, for example, during parasitic infections, most notably Leishmaniasis (7). The effects of IL-12 are mediated in large part by interferon-gamma produced by NK cells and T helper cells. Interferon-gamma is critical for the induction of IgG2a antibodies to T-dependent protein antigens (8) and IgG3 responses to T-independent antigens (9). IL-12, originally called natural killer cell stimulatory factor, is a heterodimeric cytokine (10). The expression and isolation of IL-12 protein in recombinant host cells is described in published International Patent Application WO 90/05147 (11).

Another cytokine that holds potential promise as an adjuvant is GM-CSF. GM-CSF is a particular type of colony stimulating factor (CSF). The CSFs are a family of lymphokines that induce progenitor cells found in the bone marrow to differentiate into specific types of mature blood cells. As described in U.S. Pat. No. 5,078,996 (12), which is hereby incorporated by reference, GM-CSF activates macrophages or precursor monocytes to mediate non-specific tumoricidal activity. The nucleotide sequence encoding the human GM-CSF gene has been described (12). A plasmid containing GM-CSF cDNA has been transformed into E. coli and has been deposited with the American Type Culture Collection (ATCC), 10801 University Boulevard, Manassas, Va. 20110-2209, under Accession Number 39900. As described in U.S. Pat. No. 5,229,496 (13), which is hereby incorporated by reference, the GM-CSF gene has also been inserted into a yeast expression plasmid and deposited with the ATCC under Accession Number 53157. Furthermore, as described in U.S. Pat. No. 5,073,627 (14), which is hereby incorporated by reference, a DNA sequence encoding GM-CSF having glycosylation sites removed was deposited with the ATCC under Accession Number 67231.

GM-CSF has been shown to upregulate protein molecules on antigen presenting cells known to enhance immune responses (15), and to affect Ig secretion in sort-purified murine B cells (16).

Other cytokines or lymphokines have been shown to have immune modulating activity, including, but not limited to, the interleukins 1-alpha, 1-beta, 2, 4, 5, 6, 7, 8, 10, 13, 14, 15, 16, 17 and 18, the interferons-alpha, beta and gamma, granulocyte colony stimulating factor, and the tumor necrosis factors alpha and beta.

Of concern related to the systemic administration of any cytokine or lymphokine are the biological consequences associated with cytokine or lymphokine activity. Additionally, cytokine or lymphokine effects related to the development of antigen-specific immune responses should be enhanced if local concentrations of cytokine or lymphokine are maintained.

In previous studies, GM-CSF and IL-12 have been evaluated separately; enhancement of various immune response parameters was observed.

The invention described herein demonstrates that, through the combination of an antigen, selected cytokine or lymphokine adjuvant, and the second adjuvant, MPL™ (preferably in a stable metabolizable emulsion), the immune responses specific for the antigen are enhanced.

The antigens selected for inclusion in the antigenic compositions of this invention comprise peptides or polypeptides derived from proteins, as well as fragments of any of the following: saccharides, proteins, poly- or oligonucleotides, or other macromolecular components. As used herein, a "peptide" comprises a series of at least six amino acids and contains at least one antigenic determinant, while a "polypeptide" is a longer molecule than a peptide, but does not constitute a full-length protein. As used herein, a "fragment" comprises a portion, but less than all of a saccharide, protein, poly- or oligonucleotide, or other macromolecular components. In the case of HIV, the antigenic compositions of this invention further comprise full-length HIV proteins.

The invention is exemplified in a model system using peptide antigens derived from HIV. These peptides are described in or derived from U.S. Pat. Nos. 5,013,548 (17) and 5,019,387 (18), which are hereby incorporated by reference and are now summarized. These peptides comprise amino acid sequences which correspond to a region of the HIV envelope protein against which neutralizing antibodies and T cell responses are produced.

HIV is a human retrovirus which is the causative agent of acquired immunodeficiency syndrome (AIDS). HIV infects T lymphocytes of the immune system by attaching its external envelope glycoprotein to the CD4 (T4) molecule on the surface of T lymphocytes, thus using the CD4 (T4) molecule as a receptor to enter and infect T cells. Attempts to induce a protective immune response specific for HIV-infection through immunization have b en met with very limited success. A number of approaches are currently being pursued in an attempt to determine an effective and protective vaccine strategy. These include using attenuated and recombinant bacterial vectors that express antigenic epitopes from HIV (19), recombinant adenovirus (20) or vaccinia virus vectors (21), DNA vaccines (22), and synthetic peptides that contain various T and B cell epitopes of HIV (23).

The HIV external envelope glycoprotein gp120 has been shown to be capable of inducing neutralizing antibodies in man. The recombinant protein PB1, which encodes approximately one-third of the entire gp120 molecule, has been shown to include the part of the envelope protein that induces the formation of neutralizing antibodies. However, studies in chimpanzees demonstrated that neither intact gp120 or PB1 is able to induce the production of high titers of neutralizing antibodies.

Short peptides were synthesized by conventional methods which correspond to antigenic determinants of gp120 and generate an antibody response against gp120 that neutralize the virus and induce T-helper and CTL responses against the virus.

One such peptide is the C4/V3 multiepitope-containing HIV-1$_{MN}$ peptide designated T1SP10MN(A) (+Cys), and a cysteine-deleted variant T1SP10MN(A) (−Cys). These peptides include Th, T$_{CTL}$ and B epitopes, but do not induce antibodies which interfere with CD4 binding. Previously, it has been demonstrated that these C4/V3 HIV peptides are promising candidates for the induction of immune responses when administered with CFA, or CFA-like adjuvants (24-29). These peptides contain epitopes that have previously been shown to voke CD4+ Th cell responses in both mice and humans, and it contains both a principal neutralizing determinant and a site which is recognized by CD8+ CTL in both Balb/c mice and humans that are HLA B7+. The 39 amino acid peptide has recently demonstrated both immunogenicity and safety in HIV-infected patients (28).

T1SP10MN(A) (+Cys) has the following sequence of 40 amino acids:

Lys Gln Ile Ile Asn Met Trp Gln Glu Val Gly Lys Ala Met Tyr Ala Cys Thr Arg Pro Asn Tyr Asn Lys Arg Lys Arg Ile His Ile Gly Pro Gly Arg Ala Phe Tyr Thr Thr Lys (SEQ ID NO:1) (26).

T1SP10MN(A) (−Cys) has been synthesized without the cysteine at position 17 and has the following sequence of 39 amino acids:

Lys Gln Ile Ile Asn Met Trp Gln Glu Val Gly Lys Ala Met Tyr Ala Thr Arg Pro Asn Tyr Asn Lys Arg Lys Arg Ile His Ile Gly Pro Gly Arg Ala Phe Tyr Thr Thr Lys (SEQ ID NO:2).

This cysteine residue is located outside of the functional epitopes recognized by Th cells, CTL or B cells. Other HIV peptides from various regions of the viral genome are described in U.S. Pat. No. 5,861,243 (30), U.S. Pat. No. 5,932,218 (31), U.S. Pat. No. 5,939,074 (32), U.S. Pat. No. 5,993,819 (33), U.S. Pat. No. 6,037,135 (34) and Published European Patent Application Number 671,947 (35), which are also incorporated by reference.

The HIV antigen may be a protein, polypeptide, peptide or fragment derived from said protein. The protein may be a glycoprotein such as gp41, gp120 or gp160. Alternatively, the protein may be a protein encoded by such genes as gag, pol, vif, rev, vpr, tat, nef or env. Peptides derived from such proteins will contain at least one antigenic determinant (epitope) at least six amino acids in 1 ngth.

The immune response to an HIV peptide may be enhanced by covalently linking (conjugating) the peptide to a pharmaceutically acceptable carrier molecule. Examples of suitable carrier molecules include tetanus toxoid, diphtheria toxoid, keyhole limpet haemocyanin and other peptides corresponding to T cell epitopes of the HIV gp120 glycoprotein.

It is currently felt that a successful vaccine strategy against HIV will need to elicit mucosal immunity to HIV, as well as a good CTL response. In a recent murine study using the T1SP10MN(A) multi-epitope peptide, and a mucosal adjuvant, cholera toxin, it was shown that intranasal immunization induced neutralizing serum IgG1 antibodies (36). A subsequent study also using HIV-V3 loop peptides demonstrated the induction of mucosally synthesized IgA antibody and strong cell mediated responses, including peptide-specific CTL (37). The functional role of high titers of systemic and neutralizing antibodies in the prevention of, or stabilization of HIV-infected individuals is unknown, although high titers of virus-specific antibody are believed to be important in preventing viral spread.

In a preferred embodiment of the invention, a stable oil-in-water emulsion is formulated which contains MPL™, which is then mixed with the cytokines IL-12 or GM-CSF. The data presented below demonstrate that these combinations result in high titers of HIV-neutralizing serum antibodies. The combination of MPL™ SE and GM-CSF induces high titers of antigen-specific IgG and IgA antibody in the vaginal vault of immunized femal mice. Immunization of mice with either of the T1SP10MN(A) peptides formulated with MPL™ SE and GM-CSF induced a strong cellular immune response as determined by enhanced antigen specific cellular proliferation and secretion into culture of cytokines, as well as the induction of peptide-specific CTL responses.

Generally, the antigen/adjuvant formulation of MPL™ or MPL™ SE combined with GM-CSF or IL-12 and a protein or peptide of choice induces high titers of antigen-specific and virus neutralizing antibody, a significant shift in the IgG subclass ratio to a greater proportion of complement-fixing IgG antibodies (in favor of IgG2a in mice), elevated production of cytokines and cellular proliferation from mononuclear cells in response to antigen stimulation in vitro. These properties were not observed with formulations of antigen and SE in the absence of MPL™, either with or without GM-CSF or IL-12. The formulations of this invention also induce good cellular responses as determined through induction of CTL.

A benefit of MPL™ SE is that the formulation does not induce granulomatous accumulation and inflammation at the site of injection; such injection site reactions are typically induced by water-in-oil or oil-in-water adjuvant formulations.

The ability to induce an enhanced immune response through the stimulatory effects of MPL™ in combination with GM-CSF or IL-12 in the absence of local granulomatous inflammation has not been reported with other adjuvant formulations currently proposed for treatment of HIV.

A series of studies was conducted to compare MPL™ (either with or without SE) plus GM-CSF or IL-12 to each of MPL™, SE, GM-CSF, IL-12 or CFA/IFA individually, or together with an HIV peptide. A summary of the results will now be presented, followed by a more detailed discussion.

In a first experiment, Balb/c mice immunized subcutaneously with the C4/V3 HIV peptide T1SP10MN(A) (–Cys), formulated with MPL™ SE and GM-CSF, produced serum IgG titers in excess of $10^7$ after only two injections. The antibody response was HIV-neutralizing, and demonstrated significant increases in IgG1, IgG2a, and IgG2b peptide-specific antibody titers. Spleen cells stimulated in culture with peptide released elevated levels of IL-4, IL-5, and interferon-gamma. Collectively, those findings are indicative of the induction of a balanced Th1/Th2-type response. IgG and IgA antibodies were generated that were specific for T1SP10MN(A) (–Cys) in the vaginal lavage fluids of mice immunized with MPL™ SE, and GM-CSF. These findings indicate that the combination of MPL™ SE and GM-CSF with an HIV-peptide antigen results in the induction of a favorable immune response profile.

In this first experiment, Balb/c mice immunized with the HIV peptide T1SP10MN(A) (–Cys) and an SE-containing adjuvant formulation, or GM-CSF, generated peptide specific IgG antibody titers (Table 1). An oil-in-water stable emulsion (SE) consisting of squalene, glycerol, and an emulsifying agent (phosphatidyl choline), demonstrated an ability to enhance peptide-specific IgG titers when mixed with T1SP10MN(A) (–Cys). IgG titers induced through immunization with 25 µg T1SP10MN(A) (–Cys) formulated with SE induced secondary response titers that were approximately one-fifth of those induced in mice immunized with peptide and CFA, and boosted with peptide in IFA. Recipients of CFA/IFA formulated vaccines routinely developed T1SP10MN(A) (–Cys)-specific IgG titers in response to a primary immunization. For comparative purposes, mice were immunized with 25 µg of T1SP10MN(A) (–Cys) peptide alone.

Aqueous and SE formulations of MPL™ were compared with responses induced through immunization of mice with Freund's adjuvants or the cytokines IL-12 and GM-CSF. Recipients of T1SP10MN(A) (–Cys) mixed with IL-12 generally did not generate peptide-specific antibody titers in several repeat studies. In contrast, recipients of GM-CSF or MPL™ SE plus T1SP10MN(A) (–Cys) did develop low, but readily detectable IgG antibody titers. The addition of IL-12 or GM-CSF to formulations containing MPL™ SE plus T1SP10MN(A) (–Cys) peptide induced significantly higher titers of IgG in response to immunization. Indeed, immunization of mice with MPL™ SE and GM-CSF in combination resulted in secondary response titers that were consistently greater than those determined from mice immunized with any other formulation tested. Peptide-specific IgG titers were higher than those of mice immunized with even 125 µg of T1SP10MN(A) (–Cys) formulated with Freund's adjuvants.

A desirable feature of an HIV-specific immune response is one that is balanced between cellular and humoral components. Particular immunoglobulin isotype subclasses have been correlated with the skewing of T helper cell subset types toward either Th1 or Th2 predominance. The cytokines that each of these T helper cell subsets secrete have demonstrated activity in directing IgG subclass switching. IgG subclass endpoint titers were determined from pooled sera collected two weeks after the second immunization (Table 2). Immunization of mice with T1SP10MN(A) (–Cys) alone, or formulated with either GM-CSF or IL-12, resulted in no or low IgG subclass titers in several repeat studies. IgG3 antibodies could not be detected by ELISA. Groups of mice immunized with T1SP10MN(A) (–Cys) emulsified with CFA and boosted with IFA developed predominantly an IgG1 antibody response specific for T1SP10MN(A) (–Cys). Formulations of peptide with SE, MPL™ SE, MPL™ SE plus IL-12, or MPL™ SE plus GM-CSF, also developed high titers of IgG1 antibody. Recipients of SE-formulated vaccines repeatedly demonstrated significant IgG1, but not significant IgG2a or IgG2b titers. The inclusion of MPL™ into the SE formulation resulted in enhanced IgG2a and IgG2b T1SP10MN(A) (–Cys)-specific antibody titers. The inclusion of either IL-12 or GM-CSF with MPL™ SE and T1SP10MN(A) (–Cys) resulted in a shift in the IgG1:IgG2a antibody titer ratio. Without cytokine, MPL™ SE formulated vaccines induced similar titers of IgG1 and IgG2a. Both IL-12 and GM-CSF increased the relative serum concentrations of peptide-specific IgG2a. Moreover, the combination of MPL™ SE and GM-CSF also induced a significant increase in IgG2b antibody titers specific for T1SP10MN(A) (–Cys) (47-fold compared to MPL™ SE and 74-fold compared to SE). Titers developed in mice immunized with MPL™ SE and GM-CSF together with T1SP10MN(A) (–Cys) peptide were consistently the highest of any vaccine recipient group.

Figure 1:
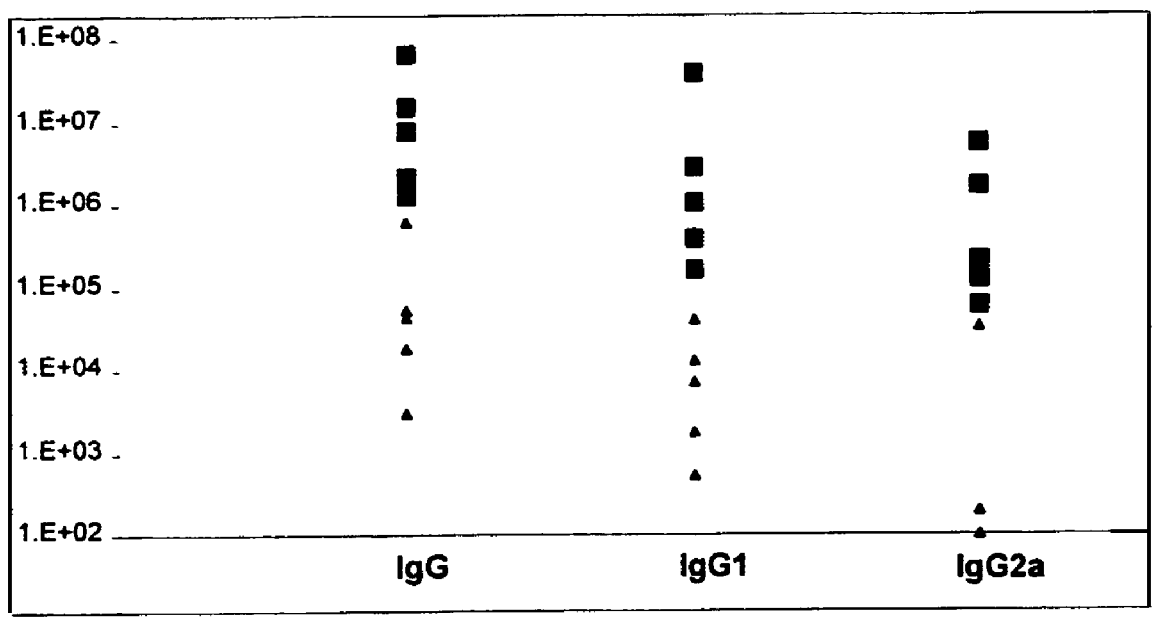
FIG. 1 depicts the reciprocal endpoint titers determined from groups of five Balb/c female mice immunized with 25 μg T1SP10MN(A) (–Cys), a multiepitope 39 amino acid peptide, formulated with CFA or IFA (triangles), or with 50 μg MPL™ 2% stable emulsion (SE) (squares). Mice were immunized on day 0 and boosted on day 28. Peptide-specific IgG, IgG1, and IgG2a titers were determined in sera collected on day 42 by ELISA.

To determine if the high titers measured from sera pooled from mice immunized with T1SP10MN(A) (–Cys), MPL™ SE, and GM-CSF were representative of the individual mice within the group, titers of individual mice within that group were compared with those of mice immunized with Freund's adjuvant formulated peptide (FIG. 1). It was determined that the mean of the individual serum titers for IgG, IgG1, and IgG2a were similar to the titers measured from serum pools (data not shown). The co-formulation of T1SP10MN(A) (–Cys) with MPL™ SE and GM-CSF resulted in titers of IgG, IgG1, and IgG2a that were significantly higher than those induced in mice immunized with CFA/IFA. All mice immunized with MPL™ SE and GM-CSF formulated peptide developed higher titers of IgG antibody than those measured from mice immunized with the CFA/IFA formulation. These results indicated that the combination of MPL™ SE with GM-CSF generated a favorable antibody response profile as determined by high titers of peptide-specific antibody, and a favorable IgG subclass distribution. This formulation routinely induced the highest T1SP10MN(A) (–Cys)-specific titers of any vaccine formulation used.

Figure 2:
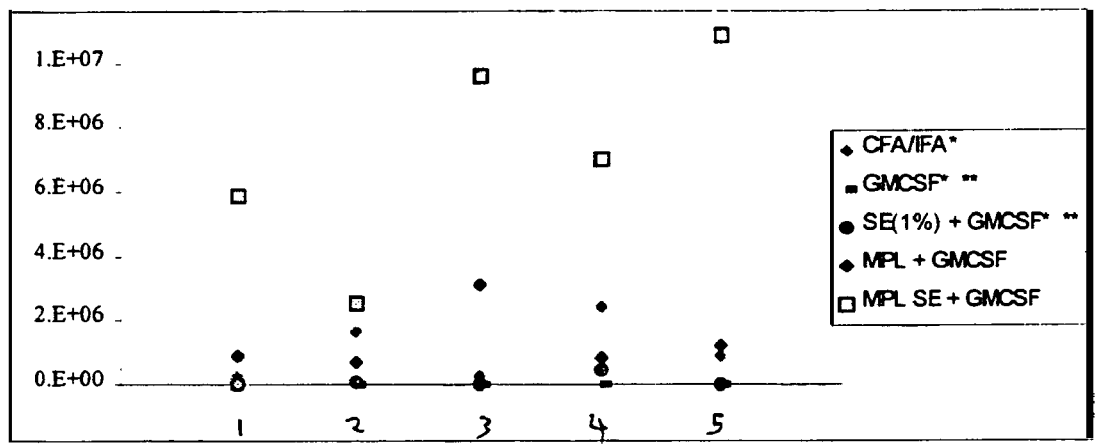
FIG. 2 depicts the effect of SE alone, MPL™ alone or MPL™ SE on the adjuvanting properties of GM-CSF on anti-T1SP10MN(A) (–Cys) IgG titers. Groups of five female Balb/c mice were immunized with 25 μg T1SP10MN(A) (–Cys) on day 0, and boosted on day 28 with the indicated adjuvant formulations. CFA and IFA were emulsified with aqueous peptide at a ratio of 1:1. GM-CSF was used at 10

A comparison was made of the anti-T1SP10MN(A) (–Cys) IgG titers of mice immunized with GM-CSF formulated together with aqueous MPL™, SE or MPL™ SE, to determine the effects of GM-CSF as an adjuvant supplement (FIG. 2). The results suggest that the combination of MPL™ SE with GM-CSF and peptide are unique in this particular embodiment in the induction of high titer antibody. MPL™ plus GM-CSF elicited titers comparable to CFA/IFA. Thus, the adjuvanting properties of MPL™ and GM-CSF appear to be synergistic when formulated together where the MPL™ is either in aqueous form or is present as a stable emulsion.

Next, T1SP10MN(A) (–Cys)-specific antibody titers were measured in pooled vaginal lavage fluid obtained from mice four weeks after a second immunization (Table 3). Mice immunized with MPL™ SE plus GM-CSF developed high titers of both IgA and IgG antibody. Antibody titers in vaginal lavage obtained from mice immunized with other formulations have not b n routinely detected. Since the ratio of IgG to IgA in the vaginal lavage favors IgG, and since sIgA was not measured, it cannot be concluded that the IgA antibody detected in vaginal lavage fluid is locally synthesized by mucosal tissues. Indeed, it is likely that the IgA and IgG titers detected are the result of transudated immunoglobulin secreted from plasma cells located distal to the vaginal mucosa.

These results demonstrated that mice immunized with an HIV-peptide T1SP10MN(A) (–Cys), formulated with MPL™ SE in combination with either IL-12 or GM-CSF had high titers of peptide-specific serum antibody.

To assess whether those antibody titers were functionally effective, sera were analyzed for their ability to inhibit the infection of cells in vitro by a laboratory adapted strain of HIV. The assay measured the reverse transcriptase activity of virus that was shed into culture supernatants from cells infected with the appropriate HIV strain. Serum from mice immunized with MPL™ SE and GM-CSF, or MPL™ SE and IL-12, both significantly reduced viral infectivity (FIG. 3). Maximum viral reverse transcriptase units ranged from 9,481 to 10,411. Sera from mice immunized with that formulation inhibited viral replication. Even at viral dilutions of only 1/20, sera from mice immunized with MPL™ SE and GM-CSF together with T1SP10MN(A) (–Cys) inhibited viral replication by approximately fifty percent. The serum neutralization titer for this formulation was determined to be greater than 1600 as compared to 71 for serum obtained from mice immunized with the MPL™ SE, IL-12 and HIV peptide formulation.

Serum anti-T1SP10MN(A) (–Cys) titers from those groups of mice were similar (albeit somewhat higher) to those elicited through immunization of mice with CFA and IFA. The sera from mice immunized with T1SP10MN(A) (–Cys) emulsified with CFA/IFA did not demonstrate HIV-neutralization in this assay. Sera from mice immunized with peptide and the combination of MPL™ SE plus GM-CSF as adjuvant, demonstrated greater neutralizing activity than any other sera. At equivalent dilutions, sera from mice immunized with MPL™ SE plus GM-CSF and the HIV peptide neutralized higher concentrations of virus than sera from recipients of other vaccine formulations.

HIV peptide-specific spleen cell proliferation in culture was then measured. As a measurement of cellular responsiveness to T1SP10MN(A) (–Cys), spleen cells were cultured in vitro with peptide or control proteins. The assay measured $^3$H-thymidine incorporated into the DNA of dividing cells (Table 4). Unlike spleen cells from mice immunized without adjuvant, spleen cells from mice immunized with T1SP10MN(A) (–Cys) formulated with SE, proliferated vigorously in response to the peptide. Spleen cells from vaccine recipients did not respond in culture to an irrelevant antigen (lysozyme), or with no antigen stimulation. All groups responded similarly to stimulation with the mitogen ConA. Within most groups, there was an indication of an antigen-specific dose dependent proliferative response. At all three doses of peptide, the highest degree of proliferation was determined for groups of mice immunized with GM-CSF co-formulated with MPL™ SE. The lowest proliferation responses were measured from spleen cells of groups of mice immunized with CFA/IFA, or IL-12 plus HIV-peptide formulated vaccines. Spleen cells from mice immunized with peptide and either SE or GM-CSF, incorporated similar levels of thymidine in culture. These results show that the co-formulation of HIV peptide with MPL™ SE together with GM-CSF, provided murine spleen cells with the highest potential for proliferation in response to in vitro presentation of antigen.

Cultured spleen cells were examined for their potential to secrete into culture supernatants the cytokines IL-4 (Table 5) and interferon-gamma (Table 6). These cytokines were measured in culture supernatants harvested after three and six days of in vitro stimulation with antigen or mitogen. Measurement of IL-4, a T helper type 2 associated cytokine, showed that whereas all groups produced detectable levels in response to stimulation with the mitogen ConA by day 3, only mice immunized with MPL™ SE, or MPL™ SE plus GM-CSF, produced IL-4 in response to peptide stimulation. Only mice immunized with MPL™ SE plus GM-CSF and T1SP10MN(A) (–Cys) secreted into culture detectable levels of IL-4 at all doses of peptide used to stimulate spleen cells.

By day six of culture, spleen cells from mice immunized with peptide together with MPL™ SE plus GM-CSF had secreted higher levels of IL-4 than those detected from mice immunized with peptide together with MPL™ SE, MPL™ SE plus IL-12, or SE. The levels of IL-4 were even higher than those induced through the stimulation of those cells in culture with ConA. Spleen cells cultured from mice immunized with MPL™ SE plus GM-CSF also secreted into culture detectable levels of IL-5 (another T helper type 2 cytokine (not shown)) in response to six days of stimulation with T1SP10MN(A) (–Cys). Spleen cells from no other groups produced detectable IL-5 in these cultures.

In response to three days of stimulation in culture with ConA, spleen cells from all groups of mice secreted detectable levels of interferon-gamma into culture (Table 6). Only cells from mice immunized with MPL™ SE or MPL™ SE plus GM-CSF produced detectable levels of interferon-gamma in response to three days of stimulation with the HIV peptide. At the end of six days of culture stimulation, higher concentrations of interferon-gamma were observed in response to both ConA and peptide. Of interest were the interferon-gamma levels measured from the culture supernatants of spleens from mice immunized with MPL™ SE, or MPL™ SE plus GM-CSF. Spleen cells from those two recipient groups secreted markedly higher concentrations of interferon-gamma into culture supernatants than did spleen cells from mice immunized with peptide together with MPL™ SE plus IL-12, or SE.

The results of the first experiment demonstrate that the inclusion of MPL™ into a stable oil-in-water emulsion, and then combining the emulsion with the HIV peptide T1SP10MN(A) (–Cys) and GM-CSF, results in the induction of neutralizing antibodies. Moreover, the co-formulation of GM-CSF with MPL™ SE and a vaccine antigen resulted in increased levels of IL-4, IL-5, and interferon-gamma secreted into culture supernatants and enhanced the proliferative response of spleen cells stimulated in culture with the immunizing antigen. That formulation also induced the highest IgG, IgG2a, and IgG2b titers of any of the vaccine formulations looked at. Only groups of mice immunized with the combination of MPL™ SE and GM-CSF together with peptide had detectable IgG and IgA titers in vaginal lavage fluid consistently over a number of repeat studies. The combination of MPL™ SE, IL-12 and peptide also resulted in increased levels of IgG1 and IgG2a titers, increased viral neutralization, increased spleen cell proliferation, and secretion of IL-4 and interferon-gamma.

The immunization of mice with any single adjuvant formulated with the HIV peptide did not produce an immune response with the properties of eliciting a neutralizing antibody.

It was often observed that immunization of mice with T1SP10MN(A) (–Cys), together with MPL™ SE or MPL™ as an aqueous formulation, induced good titers of antibody. Those formulations did not, however, consistently induce an immune response having vaginal antibody titers, neutralizing antibody titers (or strong CTL responses as described below in Experiment 8). Occasionally, MPL™ or MPL™ SE combined with peptide induced measurable titers of IgA and IgG in vaginal lavage fluid. In some studies, the addition of either IL-12, or GM-CSF to MPL™ in the vaccine formulation resulted in titers that were similar to those produced in mice immunized with CFA/IFA, or any of the MPL™ SE formulations with or without cytokine. This observation suggests that the SE form of MPL™ is not required for high titer antiserum specific for the HIV-peptide. The addition of GM-CSF to the SE vehicle conferred an increase in peptide-specific titers as compared to mice immunized with SE alone, or with SE and IL-12. In general, however, the induction of good IgG2a and IgG2b antibody titers was dependent upon the formulation of the peptide with MPL™ SE and GM-CSF. It is interesting to note that this formulation induced IgG titers that were similar to those induced through immunization with other formulations like CFA/IFA and peptide. The combination of MPL™ SE with GM-CSF and peptide was the only formulation to demonstrate the induction of both high titer neutralizing antibody and CTL (see Experiment 8). The inclusion of IL-12 with MPL™ SE and peptide also induced a favorable immune response profile. The results indicated that MPL™ SE co-formulated with cytokines GM-CSF or IL-12 imparted a qualitative difference in the antibody response as compared to immunization with CFA and IFA. That difference is believed to be attributable to elevated levels of IgG2a and IgG2b.

In a second experiment, the protocols of the first Balb/c-HIV peptide experiment were followed with minor modifications. MPL™ was also administered in aqueous form, with or without a cytokine.

Immunization of Balb/c mice with the HIV peptide T1SP10MN(A) (–Cys) without adjuvant did not induce significant titers of antibody. In contrast, formulation of peptide antigen with various adjuvant/cytokine combinations did result in the induction of high antibody titers after two immunizations.

Immunization with peptide and IL-12, or with SE only, resulted in titers that were indistinguishable from those induced without adjuvant (Table 7). Recipients of peptide co-formulated with GM-CSF had modest increases in titer. Compared with recipients of vaccine containing CFA/IFA, microfluidized MPL™ SE demonstrated similar peptide-specific titer development. Compared to recipients of CFA/IFA vaccine, MPL™ SE induced higher levels of peptide-specific IgG2a. The immunization schedules used may affect the antibody titers observed. However, immunization of mice with MPL™ (aqueous) formulated peptide induced high titers of peptide-specific antibody. Addition of GM-CSF or IL-12 to this formulation resulted in increased titers of greater than $10^6$. Thus, the combination of an HIV peptide with MPL™ and the cytokines IL-12 or GM-CSF induced high titer antibody specific for the peptide.

Only groups of mice immunized with peptide and either MPL™ and IL-12, or MPL™ SE and GM-CSF, developed relatively high titers of antibody detected from the fluids obtained from vaginal lavage (Table 8). Indeed, only that group of mice immunized with MPL™ and IL-12 with peptide produced peptide-specific IgA.

The proliferative capacity of spleen cells in culture was determined through the incorporation of thymidine in response to in vitro stimulation with peptide. The data in Table 9 are presented in such a way as to normalize the proliferation, standardizing to maximal proliferation as determined through stimulation with ConA. Spleen cells from mice immunized with MPL™ SE together with either GM-CSF or IL-12, as well as those from mice immunized with GM-CSF only, demonstrated low levels of peptide-associated proliferation. In contrast, spleen cells from mice immunized with peptide combined with MPL™ and GM-CSF demonstrated significant proliferation.

Cytokine production from spleen cells cultured in vitro was also measured. For IL-4, only mice immunized with MPL™ SE combined with GM-CSF and T1SP10MN(A) (–Cys) secreted good levels of IL-4 in response to stimulation with peptide (Table 10). For interferon-gamma, mice immunized with MPL™ SE and either GM-CSF or IL-12, or aqueous MPL™ with GM-CSF or IL-12, produced readily detectable levels of this cytokine into culture supernatants (Table 11).

Thus, the combination of cytokines GM-CSF or IL-12 with MPL™ or MPL™ SE induced high titers of antibody specific for the peptide antigen. Titers were similar to those induced through immunization of mice with peptide and CFA/IFA. The data show that these combinations also induced the highest proliferative responses of spleen cells set up in culture, and established populations of spleen cells that secreted the highest levels of interferon-gamma in response to peptide stimulation.

The results of this second experiment indicate that the coformulation of T1SP10MN(A) (−Cys) with MPL™ and the cytokines GM-CSF or IL-12 induces an immune response profile that is similar to, or better than, that induced in mice immunized with peptide and CFA, and boosted with peptide and IFA.

A histological evaluation (not shown) of the injection site two weeks after the second immunization showed that mice immunized with microfluidized MPL™ SE did not develop or maintain a mononuclear cell infiltration into the dermis. Hematoxylin/eosin stained tissues looked like those prepared from recipients of no adjuvant. In contrast, Balb/c mice immunized with CFA and IFA as adjuvants (a water-in-oil emulsion) had a large accumulation of mononuclear cells in this region. The recipients of MPL™ SE together with GM-CSF and peptide showed a noticeable, but marginal increase in mononuclear cells as compared to MPL™ SE recipients without GM-CSF. Tissues from mice immunized with GM-CSF and peptide only were not examined.

The protocols of the second experiment were followed in a third experiment, with Swiss-Webster mice used instead of Balb/c mice. Swiss-Webster mice were used to determine adjuvant effects with the HIV peptide antigen wherein the MHC-restricted helper T cell epitope would not influence the immune response. Swiss-Webster mice are an outbred strain of mice; as such, no cellular studies were performed. Only reciprocal anti-HIV peptide IgG endpoint titers and vaginal lavage endpoint reciprocal endpoint IgG and IgA antibody titers were measured in this experiment. As seen in Tables 12 and 13, the response profile was comparable to that obtained from the Balb/c mice measured in the first and second experiments.

In a fourth experiment, the protocols of the second experiment were followed with minor variations using Balb/c mice. As shown in Table 14, the adjuvant formulations of MPL™ together with either GM-CSF or IL-12 elicited a noticeably higher IgG GMT response than MPL™ alone. As shown in Table 15, the adjuvant formulation of MPL™ SE together with GM-CSF elicited a significant IgG2b subclass response. The adjuvant formulations of MPL™ together with either GM-CSF or IL-12 elicited a noticeably higher IgG2a subclass response than MPL™ alone, while the formulations of MPL™ SE together with either GM-CSF or IL-12 elicited a higher IgG2a subclass response than MPL™ alone. As shown in Table 16, the adjuvant formulations of MPL™ together with either GM-CSF or IL-12 elicited a noticeably higher IgG titers in vaginal lavage fluids than MPL™ alone. Finally, as shown in FIG. 4, the adjuvant formulations of MPL™ together with either GM-CSF or IL-12, as well as the formulations of MPL™ SE together with either GM-CSF or IL-12, demonstrated a greater proliferation of spleen cells than MPL™ alone or MPL™ SE alone, respectively.

In a fifth experiment, the protocols of the second experiment were followed with minor variations using Balb/c mice; IL-12 was not included in the adjuvant formulations. As shown in Table 17, adjuvant formulations containing both MPL™ and GM-CSF elicited noticeably higher IgG2a and IgG2b responses than MPL™ alone. Furthermore, adjuvant formulations containing both MPL™ and GM-CSF elicited noticeably higher responses for all IgG subclasses than MPL™ alone.

In a sixth experiment, the protocols of the second experiment were followed with minor variations using Balb/c mice; IL-12 was not included in the adjuvant formulations. The HIV peptide was 40 amino acids in length, because of the presence of a cysteine at amino acid position 17. As shown in Table 18, adjuvant formulations containing both MPL™ SE and GM-CSF elicited significantly higher responses for all IgG subclasses than MPL™ alone and noticeably higher responses for all subclasses than MPL™ SE alone.

In a seventh experiment, the protocols of the sixth experiment were followed with minor variations using Balb/c mice; IL-12 was not included in the adjuvant formulations. As shown in Table 19, adjuvant formulations containing both MPL™ SE and GM-CSF elicited noticeably higher responses for all IgG subclasses than MPL™ SE, and adjuvant formulations containing both MPL™ and GM-CSF elicited noticeably higher responses for all IgG subclasses than MPL™ alone.

In an eighth experiment, as a measure of functional cell mediated immunity, the ability of spleen cells from mice immunized with MPL™ SE, or MPL™ SE plus GM-CSF formulated together with the multi-epitope peptide T1SP10MN(A) (+Cys) to generate $HIV_{MN}$-specific CTL responses was assessed.

As shown in FIG. 5, spleen cells from mice immunized with MPL™ SE, or MPL™ SE plus GM-CSF demonstrated low activity toward target cells that were either unlabelled or pulse-labeled with the IIIB CTL epitope. Spleen cells from mice immunized with T1SP10MN(A) (+Cys) formulated with MPL™ SE and GM-CSF together induced good $HIV_{MN}$-specific CTL activity after a single immunization. $HIV_{MN}$-specific CTL-mediated target cell lysis was markedly enhanced when measured seven days after secondary immunization (FIG. 5). In separate experiments, mice immunized without adjuvant did not induce a CTL response. Mice immunized with aqueous MPL™ and peptide generated low (<30%) peptide-specific CTL responses.

One difficulty is assessing the potential efficacy of immunogenic compositions against HIV is that non-human primates infected with HIV do not develop AIDS-like symptoms. Thus, a potential animal model does not mimic the human symptomology caused by HIV. Fortunately, non-human primates infected with Simian immunodeficiency virus (SIV), which is closely related to HIV, do develop AIDS-like symptoms.

This enables SIV antigens to be assessed in non-human primates. The SIV antigen may be a protein, polypeptide, peptide or fragment derived from said protein. The protein may be a glycoprotein such as gp41, gp120 or gp160. Alternatively, the protein may be a protein encoded by such genes as gag, pol, vif, rev, vpr, tat, nef or env. Peptides derived from such proteins will contain at least one antigenic determinant (epitope) at least six amino acids in length.

Analogously to HIV, multiepitope SIV peptides are used in non-human primates. A study was conducted to assess whether various peptides in combination with MPL™ SE and GM-CSF could elicit a CTL response. Rhesus macaques were immunized subcutaneously at weeks 0, 4, 8 and 18 with MPL™ SE and GM-CSF together with either of the following sets of three peptides (see Table 20):

(1) Each peptide contained a Mamu A*01 restricted CTL epitope as follows:

Cys Thr Pro Tyr Asp Ile Asn Gln Met (SEQ ID NO:3) (gag) (38,39)

Ser Thr Pro Pro Leu Val Arg Leu Val (SEQ ID NO:4) (pol) (40)

Tyr Ala Pro Pro Ile Ser Gly Gln Ile (SEQ ID NO:5) (env) (40)

(2) Alternatively, each of these three peptides was linked to a promiscuous T-helper epitope having the following sequence:

Glu Leu Tyr Lys Tyr Lys Val Val Lys Ile Glu Pro Leu Gly Val Ala Pro Thr Lys Ala (SEQ ID NO:6) (adapted from 41).

Thus, the three peptides had the following sequences:

Glu Leu Tyr Lys Tyr Lys Val Val Lys Ile Glu Pro Leu Gly Val Ala Pro Thr Lys Ala Cys Thr Pro Tyr Asp Ile Asn Gln Met (SEQ ID NO:7)

Glu Leu Tyr Lys Tyr Lys Val Val Lys Ile Glu Pro Leu Gly Val Ala Pro Thr Lys Ala Ser Thr Pro Pro Leu Val Arg Leu Val (SEQ ID NO:8)

Glu Leu Tyr Lys Tyr Lys Val Val Lys Ile Glu Pro Leu Gly Val Ala Pro Thr Lys Ala Tyr Ala Pro Pro Ile Ser Gly Gln Ile (SEQ ID NO:9).

Heparinized blood was collected every two weeks and peripheral blood mononuclear cells analyzed for CTL by the $^{51}$Cr Release assay, tetramer staining of fresh peripheral blood mononuclear cells (PBMC) and tetramer staining of cultured PBMC. Tetramer staining of fresh PBMC and cytolytic killing by $^{51}$Cr release did not reveal any activity. However, immunization of Rhesus macaques with Mamu A*01 restricted Th/CTL peptide cocktails formulated with MPL™ SE and GM-CSF resulted in the detection of tetramer positive CD8 positive T cells. The results presented in Tables 21-24 are shown as the percent positive, tetramer positive CD8+ (Tables 21-23) or CD4+ (Table 24) T cells detected in PBMC cultured with the respective peptide for 11 days.

Overall, all four Mamu A*01 positive animals immunized with the CTL epitopes either with (Rh 55, Rh 142) or without (Rh 73, Rh 80) the Th epitopes demonstrated CD8 positive tetramer positive cells specific for either gag, pol or env. As expected, no tetramer positive CD8 cells were detected in the Mamu A*01 negative animals (Rh 41, Rh47). SIV gag and env specific immune responses were seen after priming while pol specific Tetramer positivity was observed after boosting. Because the final booster dose at 18 weeks did not further elevate the response, data are not presented after 14 weeks in Tables 21-24.

In summary, immunization of Rhesus macaques with Mamu*A01 restricted Th/SIV gag, pol and env CTL epitope peptide cocktails adjuvanted with MPL™ SE and human GM-CSF elicited cellular responses as evidenced by the sensitive and specific tetramer assay.

The Porin B protein of *Neisseria gonorrhoeae*, also known as the PIB protein, has been expressed recombinantly (42, which is hereby incorporated by reference), and is a candidate antigen for prevention or treatment of infections caused by *Neisseria gonorrhoeae*.

A series of studies was conducted to compare MPL™ (either with or without SE) plus GM-CSF or IL-12, to MPL™ (either with or without SE) alone, together with a modified version of the Porin B protein of *Neisseria gonorrhoeae*, in which 16 amino acids at the amino-terminus are from a phage, followed by the mature form of the Porin B protein. A summary of the results will now be presented.

In a first experiment, Swiss-Webster mice immunized subcutaneously in the rump with recombinant Porin B protein generated antigen-specific antibody titers, demonstrating that Porin B protein is a viable candidate antigen. Addition of GM-CSF to MPL™ and the Porin B protein resulted in elevated serum antibody IgG and IgG2a titers compared to recipients of MPL™ and the Porin B protein (see Tables 25 and 26).

In a second experiment, Swiss-Webster mice immunized subcutaneously in the rump with the Porin B protein plus IL-12 and MPL™ or MPL™ SE induced higher antigen-specific antibody (particularly IgG) compared to recipients of the Porin B protein plus MPL™ or MPL™ SE. Higher titers were observed after both the primary and secondary immunizations. The inclusion of IL-12 in the formulations resulted in an approximate ten-fold increase in IgG titers measured in vaginal lavage fluid (see Table 27).

The purified native fusion (F) protein of Human Respiratory syncytial virus (RSV) in the native dimeric form is a candidate antigen for prevention of infections caused by RSV (43, which is hereby incorporated by reference).

A series of studies was conducted to compare MPL™ (either with or without SE) plus GM-CSF or IL-12 to each of MPL™ (either with or without SE), aluminum phosphate or Stimulon™ QS-21 individually, together with the purified native F protein of RSV. A summary of the results will now be presented.

In a first experiment, Balb/c mice immunized intramuscularly with the native RSV F protein generated antigen-specific antibody titers, demonstrating that the F protein is a viable candidate antigen. Addition of GM-CSF to MPL™ induced higher endpoint titers than MPL™ alone against F protein after both the primary and secondary immunizations (see Table 28), and also induced an enhanced cellular response to in vitro stimulation of spleen cells than MPL™ alone (see Table 29). Addition of GM-CSF to MPL™ SE resulted in an elevated primary IgG response to F protein than MPL™ SE alone (see Table 28).

A second experiment repeated the protocol of the first experiment. Addition of GM-CSF to MPL™ induced higher endpoint titers than MPL™ alone against F protein after both the primary and secondary immunizations (see Table 30). Addition of GM-CSF to MPL™ SE also induced higher endpoint titers than MPL™ SE alone against F protein after the primary immunization (see Table 30). The addition of GM-CSF to formulations of F protein plus MPL™ or MPL™ SE induced a higher percentage of RSV-specific splenic CTL activity than that induced by formulations lacking GM-CSF, as measured from the spleen cells of immunized mice (see Table 31).

A third experiment substituted IL-12 for GM-CSF. The co-formulation of IL-12 with MPL™ induced higher titers of IgG after priming immunization, as compared to the delivery of F protein with MPL™ alone (see Table 32). However, the addition of IL-12 to MPL™ or MPL™ SE had no effect on the RSV-specific CTL activity measured after in vitro stimulation of effector cells (see Table 33).

One study was conducted to compare MPL™ (either with or without SE) plus GM-CSF to MPL™ (either with or without SE) individually, together with the Influenza virus NP (nucleocapsid) protein. There were insufficient quantities of the NP to conduct experiments to measure antibody titers. Mice immunized with the NP peptide with or without adjuvants were analyzed for spleen cell responses to antigen stimulation 14 days after the final immunization. The inclusion of GM-CSF in the formulations containing MPL™ or MPL™ SE resulted in a marked reduction of CTL activity (data not shown).

It is unclear why this anomalous result was obtained. There may have been technical problems in the conduct of the assay.

The antigenic compositions of the present invention modulate the immune response by improving the vertebrate host's antibody response and cell-mediated immunity after administration of an antigenic composition comprising a selected antigen from a pathogenic virus, bacterium fungus or parasite, and an effective adjuvanting amount of MPL™ (in an aqueous or stable emulsion form) combined with a cytokine or lymphokine, in particular GM-CSF or IL-12. Other cytokines or lymphokines have been shown to have immune modulating activity, including, but not limited to, the interleukins 1-alpha, 1-beta, 2, 4, 5, 6, 7, 8, 10, 13, 14, 15, 16, 17 and 18, the interferons-alpha, beta and gamma, granulocyte colony stimulating factor, and the tumor necrosis factors alpha and beta.

Agonists of or antagonists to said cytokines or lymphokines are also within the scope of this invention. As used herein, the term "agonist" means a molecule that enhances the activity of, or functions in the same way as, said cytokines or lymphokines. An example of such an agonist is a mimic of said cytokines or lymphokines. As used herein, the term "antagonist" means a molecule that inhibits or prevents the activity of said cytokines or lymphokines. Examples of such antagonists are the soluble IL-4 receptor and the soluble TNF receptor.

As used herein, the term "effective adjuvanting amount" means a dose of the combination of adjuvants d scribed herein, which is suitable to elicit an increased immune response in a vertebrate host. The particular dosage will depend in part upon the age, weight and medical condition of the host, as well as on the method of administration and the antigen. In a preferred embodiment, the combination of adjuvants will utilize MPL™ in the range of 1-100 µg/dose. Suitable doses are readily determined by persons skilled in the art. The antigenic compositions of this invention may also be mixed with immunologically acceptable diluents or carriers in a conventional manner to prepare injectable liquid solutions or suspensions.

The antigenic compositions of this invention are administered to a human or non-human vertebrate by a variety of routes, including, but not limited to, intranasal, oral, vaginal, rectal, parenteral, intradermal, transdermal (see, e.g., International application WO 98/20734 (44), which is hereby incorporated by reference), intramuscular, intraperitoneal, subcutaneous, intravenous and intraarterial. The amount of the antigen component or components of the antigenic composition will vary depending in part upon the identity of the antigen, as well as upon the age, weight and medical condition of the host, as well as on the method of administration. Again, suitable doses are readily determined by persons skilled in the art. It is preferable, although not required, that the antigen and the combination of adjuvants be administered at the same time. The number of doses and the dosage regimen for the antigenic composition are also readily determined by persons skilled in the art. In some instances, the adjuvant properties of the combination of adjuvants may reduce the number of doses needed or the time course of the dosage regimen.

The combinations of adjuvants of this invention are suitable for use in antigenic compositions containing a wide variety of antigens from a wide variety of pathogenic microorganisms, including but not limited to those from viruses, bacteria, fungi or parasitic microorganisms which infect humans and non-human vertebrates, or from a cancer cell or tumor cell. The antigen may comprise peptides or polypeptides derived from proteins, as well as fragments of any of the following: saccharides, proteins, poly- or oligonucleotides, cancer or tumor cells, allergens, Aβ protein or peptide thereof, or other macromolecular components. In some instances, more than one antigen is included in the antigenic composition.

Desirable viral vaccines containing the adjuvant combinations of this invention include those directed to the prevention and/or treatment of disease caused by, without limitation, Human immunodeficiency virus, Simian immunodeficiency virus, Respiratory syncytial virus, Parainfluenza virus types 1-3, Influenza virus, Herpes simplex virus, Human cytomegalovirus, Hepatitis A virus, Hepatitis B virus, Hepatitis C virus, Human papillomavirus, poliovirus, rotavirus, caliciviruses, Measles virus, Mumps virus, Rubella virus, adenovirus, rabies virus, canine distemper virus, rinderpest virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

Desirable bacterial vaccines containing the adjuvant combinations of this invention include those directed to the prevention and/or treatment of disease caused by, without limitation, *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare* complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum*.

Desirable vaccines against fungal pathogens containing the adjuvant combinations of this invention include those directed to the prevention and/or treatment of disease caused by, without limitation, *Aspergillus, Blastomyces, Candida, Coccidiodes, Cryptococcus* and *Histoplasma*.

Desirable vaccines against parasites containing the adjuvant combinations of this invention include those directed to the prevention and/or treatment of disease caused by, without limitation, *Leishmania major, Ascaris, Trichuris, Giardia, Schistosoma, Cryptosporidium, Trichomonas, Toxoplasma gondii* and *Pneumocystis carinii*.

Desirable vaccines for eliciting a therapeutic or prophylactic anti-cancer effect in a vertebrate host, which contain the adjuvant combinations of this invention, include those utilizing a cancer antigen or tumor-associated antigen including, without limitation, prostate specific antigen, carcino-embryonic antigen, MUC-1, Her2, CA-125 and MAGE-3.

Desirable vaccines for moderating responses to allergens in a vertebrate host, which contain the adjuvant combinations of this invention, include those containing an allergen or fragment thereof. Examples of such allergens are described in U.S. Pat. No. 5,830,877 (45) and published International Patent Application Number WO 99/51259 (46), which are hereby incorporated by reference, and include pollen, insect venoms, animal dander, fungal spores and drugs (such as penicillin). The vaccines interfere with the production of IgE antibodies, a known cause of allergic reactions.

Desirable vaccines for preventing or treating disease characterized by amyloid deposition in a vertebrate host, which contain the adjuvant combinations of this invention, include those containing portions of Aβ protein or peptide thereof. This disease is referred to variously as Alzheimer's disease, amyloidosis or amyloidogenic disease. The β-amyloid peptide (also referred to as Aβ peptide) is a 42 amino acid fragment of Aβ protein, which is generated by processing of Aβ protein by the β and γ secretase enzymes, and has the following sequence:

Asp Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala (SEQ ID NO:10).

In some patients, the amyloid deposit takes the form of an aggregated Aβ peptide. Surprisingly, it has now been found that administration of isolated Aβ peptide induces an immune response against the Aβ peptide component of an amyloid deposit in a vertebrate host (47). Thus, the vaccines of this invention include the adjuvant combinations of this invention plus Aβ peptide, as well as fragments of Aβ peptide and antibodies to Aβ peptide or fragments thereof. One such fragment of Aβ peptide is the 28 amino acid peptide having the following sequence (48):

Asp Ala Glu Phe Arg His Asp Ser Gly Tyr Glu Val His His Gln Lys Leu Val Phe Phe Ala Glu Asp Val Gly Ser Asn Lys (SEQ ID NO:11).

In the case of HIV and SIV, the antigenic compositions comprise at least one protein, polypeptide, peptide or fragment derived from said protein. In some instances, multiple HIV or SIV proteins, polypeptides, peptides and/or fragments are included in the antigenic composition.

The adjuvant combination formulations of this invention are also suitable for inclusion as an adjuvant in polynucleotide vaccines (also known as DNA vaccines). Such vaccines may further include facilitating agents such as bupivicaine (see U.S. Pat. No. 5,593,972 (49), which is hereby incorporated by reference).

In order that this invention may be better understood, the following examples are set forth. The examples are for the purpose of illustration only and are not to be construed as limiting the scope of the invention.

EXAMPLES

Experiment 1

Immunization of Balb/c Mice with an HIV Peptide and Various Adjuvants

Example 1

Materials and Methods

Animals

Female Balb/c mice, aged 7-9 weeks, were purchased from Taconic Farms, Inc. (Germantown, N.Y.). All mice were housed in a facility approved by the American Association for Accreditation of Laboratory Animal Care. Mice were acclimatized to the housing facility for one week prior to initiation of studies.

Peptides

The sequence of the multiepitope HIV-1-$_{MN}$ peptide T1SP10MN(A) (–Cys) is as follows:

Lys Gln Ile Ile Asn Met Trp Gln Glu Val Gly Lys Ala Met Tyr Ala Thr Arg Pro Asn Tyr Asn Lys Arg Lys Arg Ile His Ile Gly Pro Gly Arg Ala Phe Tyr Thr Thr Lys (SEQ ID NO:2). This peptide has been previously described (28,29), and contains sequences from HIV-1 gp120 that evoke CD4$^+$ Th cell responses in both mice and humans, a principal neutralizing determinant, and a site recognized by CD8$^+$ CTL in Balb/c mice. The peptide was provided by Dr. R. Scearce (Duke University, Durham, N.C.). For CTL analysis, peptides corresponding to the CTL epitope within the V3 loop of HIV-1-$_{IIIB}$ (Arg Gly Pro Gly Arg Ala Phe Val Thr Ile (SEQ ID NO:12), H-2D$^d$ restricted) or HIV-1-$_{MN}$ (11 Gly Pro Gly Arg Ala Phe Tyr Thr Thr (SEQ ID NO:13), H-2D$^d$ restricted), were purchased from Genosys Biotechnologies Inc. (The Woodlands, Tex.). Peptides were solubilized in sterile water, and diluted in appropriate buffers, or cell culture medium, prior to use.

Adjuvants

All MPL™-containing adjuvant preparations were obtained from Ribi ImmunoChem Research, Inc. (Hamilton, Mont.). MPL™ was prepared as an aqueous formulation using triethanolamine (Sigma, St. Louis, Mo.). After solubilization, MPL™ was sonicated as per manufacturer's instructions to generate an opalescent/clear solution which was sterile filtered. MPL™ SE was provided as a preformulated squalene based oil-in-water (1-2% oil) emulsion, having MPL™ concentrations ranging from 0-250 μg/ml. Aluminum phosphate was prepared in-house. Freund's complete adjuvant (CFA) and incomplete adjuvant (IFA) were purchased from Difco Laboratories, Detroit, Mich. T1SP10MN(A) peptides and Freund's adjuvants were emulsified in a 1:1 ratio using two linked syringes. Recombinantly expressed murine IL-12 was provided by Genetics Institute (Cambridge, Mass.). Recombinant murine GM-CSF was supplied by Immunex (Seattle, Wash.), provided by R&D Systems (Minneapolis, Minn.), or purchased from Biosource International (Camarillo, Calif.) as a carrier-free lyophilized powder.

Immunizations

Mice were immunized subcutaneously in the rump, in a total volume of 0.2 ml equally divided on each side of the tail. Immunizations were administered at varying time intervals, as indicated below. Antigen and cytokines were diluted in phosphate buffered saline to the appropriate concentrations and formulated with adjuvants less than 16 hours prior to immunization, under sterile conditions. Vaccines were mixed by gentle agitation, and stored at 4° C. Formulations were mixed by vortex immediately prior to immunization.

Sample Collections

Animals were bled prior to initial immunization, and at indicated time points. Serum was analyzed from individual mice, or as pools from mice within groups. Vaginal lavage was performed on euthanized mice to assess antibody levels. This was accomplished by instillation of 75:1 RPMI-10 into the vaginal vault of female mice using a 200:1 pipette. The vault was washed by repeated delivery and removal of fluid, which was then added to 10:1 of FBS. Vaginal lavage were analyzed as pools.

Cell Preparations

For proliferation assays and in vitro cytokine analysis, spleen cells were obtained from mice at the indicated time points. Single cell suspensions were prepared from pools of 3-5 mice as indicated in Results. For proliferation and cytokine analysis, cells were suspended in round bottom 96 well culture plates precoated overnight with HIV peptide antigens, control proteins, or RPMI-10 only. Spleen cells were added at $5\times10^5$ cells/well using culture medium having 2× supplements. Cell culture supernatants were harvested from triplicate wells for cytokine analysis three or six days after culture initiation. Immediately after supernatant harvest, cultures were pulsed with $^3$H-thymidine for 18-24 hours, and harvested to quantify cell proliferation.

Enzyme-Linked Immunosorbent Assays

For analysis of HIV peptide-specific antibody and subclass distribution, peptide was suspended in either carbonate buffer (15 mM $Na_2CO_3$, 35 mM $NaHCO_3$, pH 9.6), or PBS, at a concentration of 1 μg/ml and plated to 96 well microtiter plates (Nunc) in a volume of 100:1. After overnight incubation at 37° C., plates were washed, and blocked (0.1% gelatin/PBS) at room temperature for 2-4 hours. ELISA plates were washed with wash buffer (PBS, 0.1% Tween™20) before addition of serially diluted serum (PBS, 0.1% gelatin, 0.05% Tween™20, 0.02% sodium azide). After a four hour incubation, wells were washed and appropriate dilutions of biotinylated anti-isotype/subclass antibodies were added for incubation at 4° C. overnight. Wells were washed and incubated with strepavidin-conjugated horseradish peroxidase. After incubation, wells were washed, and developed with ABTS. Wells were read at 405 nm. Titers were standardized using control sera.

For cytokine analysis, cell culture supernatants were added to wells coated with BVD6-11B11 (for anti-IL4), or R4-6A2 (for interferon-gamma). After incubation and washing, wells were developed using biotin-labeled BVD6-24G2 (for IL4) or XMG 1.2 (for interferon-gamma). The concentration of cytokines was determined using a standard curve prepared from recombinant murine interferon-gamma or interleukin-4. All cytokine reagents were purchased from Pharmingen (San Diego, Calif.).

HIV-1$_{MN}$ Neutralization Assays

Neutralization assays were performed in the laboratory of Dr. Thomas Matthews at Duke University. Briefly, coded serum was provided for neutralization of the laboratory virus isolate HIV-1$_{MN}$ (NIH). The assay was performed essentially as previously described (25). Briefly, dilutions of test sera were aliquoted in wells of a 96-well microtiter plate (25:1/well). An equal volume of serially diluted virus stock was added to each well. After incubation, the virus/antibody mixture was added to AA5 target cells. Cells were cultured in 96-well microtiter plates by addition of fresh medium every other day. Seven days post-infection, supernatants were assessed for the presence of viral reverse transcriptase as a measurement of viral replication, and successful infection or inhibition thereof.

Example 2

Reciprocal Anti-T1SP10MN(A) IgG Endpoint Titers

Reciprocal anti-HIV peptide-specific IgG endpoint titers were measured from pooled serum (n=5 Balb/c) at the indicated time points after initial immunization. Mice were immunized subcutaneously in the rump with 25 μg of T1SP10MN(A) (–Cys), unless otherwise indicated, on day 0, and on day 27. For recipients of Freund's adjuvants, mice were primed with peptide emulsified in CFA, and boosted with IFA. MPL™ SE was provided as an emulsion containing 2% squalene oil and 50 μg MPL™ per dose. SE is an oil-in-water emulsion vehicle consisting of squalene, glycerol, and an emulsifying agent. Recombinant murine IL-12 was delivered at 50 ng/mouse. Recombinant murine GM-CSF was delivered at 10 μg/mouse. The results are given in Table 1.

TABLE 1

Reciprocal anti-T1SP10MN(A) (-Cys) IgG endpoint titers

| Adjuvant | μg HIV peptide | Endpoint Titers | | |
| --- | --- | --- | --- | --- |
| | | WEEK 4 | WEEK 6 | WEEK 8 |
| None | 25 | <100 | <100 | <100 |
| CFA/IFA | 25 | 23,998 | 137,683 | 313,200 |
| rIL-12 | 25 | <100 | <100 | <100 |
| GM-CSF | 25 | <100 | 17,579 | 12,537 |
| SE | 25 | <100 | 171,923 | 76,479 |
| MPL ™ SE | 25 | <100 | 104,331 | 79,021 |
| MPL ™ SE + rIL-12 | 25 | <100 | 1,313,330 | 631,688 |
| MPL ™ SE + GM-CSF | 25 | 14,824 | >10,000,000 | 3,752,870 |

Example 3

Reciprocal Anti-T1SP10MN(A) (–Cys) IgG Endpoint Subclass Titers

Reciprocal endpoint IgG subclass titers were measured from pooled serum (n=5 Balb/c) six weeks after initial immunization, two weeks after secondary immunization. Mice were immunized subcutaneously in the rump with 25 μg of peptide, unless otherwise indicated. For recipients of Freund's adjuvants, mice were primed with peptide emulsified in complete Freund's adjuvant, and boosted with incomplete Freund's adjuvant on weeks four and six. MPL™ SE was provided as an emulsion containing 2% squalene oil and 50 μg MPL™ per dose. SE is an oil-in-water emulsion vehicle consisting of squalene, glycerol, and an emulsifying agent. Recombinant murine IL-12 was delivered at 50 ng/mouse. Recombinant murine GM-CSF was delivered at 10 μg/mouse. The results are given in Table 2.

TABLE 2

Reciprocal anti-T1SP10MN(A) (-Cys) IgG endpoint subclass titers

| Adjuvants | μg HIV peptide | Endpoint Titers | | |
| --- | --- | --- | --- | --- |
| | | IgG1 | IgG2a | IgG2b |
| None | 25 | <100 | <100 | <100 |
| CFA/IFA | 25 | 29,907 | 143 | 798 |
| rIL-12 (.05) | 25 | <100 | <100 | <100 |
| GM-CSF (10) | 25 | 1,783 | <100 | <100 |
| SE (2%) | 25 | 74,293 | <100 | 3,331 |
| MPL ™ (50) SE (2%) | 25 | 11,441 | 10,176 | 5,280 |
| MP ™ (50) SE (2%) + rIL-12 (.05) | 25 | 169,278 | 27,161 | 2,303 |
| MPL ™ (50) SE (2%) + GM-CSF (10) | 25 | 3,494,862 | 954,707 | 245,828 |

Example 4

Vaginal Lavage IgG and IgA Anti-T1SP10MN(A) (–Cys) Antibody Titers

Vaginal IgG and IgA anti-peptide antibody titers were measured from lavage obtained 2 weeks after final immunization. Groups of 5 Balb/c female mice were immunized with 25 μg T1SP10MN(A) (–Cys) and the indicated adjuvant formulations on days 0, 28, and 42. Vaginal antibody titers were determined from pool d lavage fluid. The results are given in Table 3.

TABLE 3

| Vaginal Lavage IgG and IgA anti-T1SP10MN(A) (–Cys) Antibody Titers | | |
|---|---|---|
| Adjuvant | IgG | IgA |
| None | <20 | <20 |
| CFA/IFA | 20 | <20 |
| rIL-12 (.05) | <20 | <20 |
| GM-CSF (10) | <20 | <20 |
| MPL ™ (50) SE (2%) | <20 | <20 |
| MPL ™ (50) SE (2%) + rIL-12 (.05) | 24 | <20 |
| MPL ™ (50) SE (2%) + GM-CSF (10) | 1,125 | 113 |
| SE (2%) | <20 | <20 |

Example 5

Spleen Cell Proliferation

Proliferation of spleen cells from mice immunized with T1SP10MN(A) (–Cys) and various adjuvant formulations was measured. Groups of five Balb/c female mice were immunized with 25 µg T1SP10MN(A) (–Cys) and the indicated adjuvants on days 0 and 28. Spleen cells were established in culture on day 56, and harvested for measurement of $^3$H-thymidine incorporation 96 hours later. Mice were immunized with 50 ng IL-12, 10 ng GM-CSF, 50 µg MPL™ in an aqueous formulation, or as a stable emulsion with 2% SE. Data are presented as the delta cpm values as compared to proliferation values measured from cells grown in culture without stimulation. Background stimulation counts were <800 cpm. The results are given in Table 4.

TABLE 4

| | Spleen cell proliferation | | | | | |
|---|---|---|---|---|---|---|
| | Antigen | | | | | |
| Adjuvant | HIV Peptide 10 µg/ml | HIV Peptide 3.3 µg/ml | HIV Peptide 1.1 µg/ml | Con A 1 µg/ml | Lysozyme 30 µg/ml | Medium 0 µg/ml |
| None | 2,065 | 2,373 | 801 | 50,019 | 628 | — |
| CFA/IFA | 1,236 | 878 | 641 | 53,781 | — | — |
| IL-12 | 809 | 692 | 308 | 42,612 | — | — |
| GM-CSF | 25,821 | 19,784 | 14,249 | 55,578 | — | — |
| MPL ™ SE | 46,275 | 41,675 | 40,998 | 45,443 | 413 | — |
| MPL ™ SE + IL-12 | 26,560 | 19,907 | 9,600 | 38,989 | 934 | — |
| MPL ™ SE + GM-CSF | 74,909 | 66,257 | 62,798 | 37,775 | 366 | — |
| SE | 31,327 | 23,396 | 20,480 | 66,949 | — | — |

Example 6

Secretion of IL-4 by Spleen Cells

Interleukin-4 secreted into culture by spleen cells stimulated with 25 µg T1SP10MN(A) (–Cys) was measured. Spleen cells were harvested from pools of five Balb/c female mice and cultured with the indicated antigenic stimuli (50 ng IL-12, 10 µg GM-CSF, 50 µg MPL™ as indicated) for either three or six days. Interleukin-4 levels were determined by ELISA, and compared to a standard having a known concentration. Blank wells indicate that the assay could not detect Interleukin-4 from those culture conditions. The lower limit of detection sensitivity was 22 Units/ml. The results are given in Table 5.

TABLE 5

| | Secretion of IL-4 by Spleen Cells Three Day Cultures: | | | | | |
|---|---|---|---|---|---|---|
| | Antigen | | | | | |
| Adjuvant | HIV Peptide 10 µg/ml | HIV Peptide 3.3 µg/ml | HIV Peptide 1.1 µg/ml | Con A 1 µg/ml | Lysozyme 30 µg/ml | Medium 0 µg/ml |
| None | | | | 149 | | |
| CFA/IFA | | | | 156 | | |
| IL-12 | | | | 156 | | |
| GM-CSF | | | | 159 | | |
| MPL ™ SE | 297 | 79 | 90 | 134 | | |
| MPL ™ SE + IL-12 | | | | 77 | | |

TABLE 5-continued

Secretion of IL-4 by Spleen Cells
Three Day Cultures:

| Adjuvant | Antigen | | | | | |
|---|---|---|---|---|---|---|
| | HIV Peptide 10 µg/ml | HIV Peptide 3.3 µg/ml | HIV Peptide 1.1 µg/ml | Con A 1 µg/ml | Lysozyme 30 µg/ml | Medium 0 µg/ml |
| MPL™ SE + GM-CSF | 142 | 151 | 102 | 146 | | |
| SE | | | | 197 | | |

Example 7

Secretion of Interferon-Gamma by Spleen Cells

Interferon-gamma secreted into culture by spleen cells stimulated with 25 µg T1SP10MN(A) (–Cys). Spleen cells were harvested from pools of five Balb/c female mice and cultured with the indicated antigenic stimuli (the same as in Example 6) for either three or six days. Interferon-gamma levels were determined by ELISA, and compared to a standard having a known concentration. Blank wells indicate that the assay could not detect Interferon-gamma from those culture conditions. The lower limit of detection sensitivity was 4 picograms/ml. The results are given in Table 6.

TABLE 6

Secretion of Interferon-gamma by Spleen Cells

| Adjuvant | Antigen | | | | | |
|---|---|---|---|---|---|---|
| | HIV Peptide 10 µg/ml | HIV Peptide 3.3 µg/ml | HIV Peptide 1.1 µg/ml | Con A 1 µg/ml | Lysozyme 30 µg/ml | Medium 0 µg/ml |
| Three Day Cultures: | | | | | | |
| None | | | | 23.0 | | |
| CFA/IFA | | | | 5.0 | | |
| IL-12 | | | | 5.9 | | |
| GM-CSF | | | | 17.6 | | |
| MPL™ SE | 6.6 | 4.2 | 4.3 | 18.2 | | |
| MPL™ SE + IL-12 | | | | 9.2 | | |
| MPL™ SE + MG-CSF | 11.5 | 5.1 | 5.3 | 14.6 | | |
| SE | | | | 8 | | |
| Six Day Cultures: | | | | | | |
| Non | | | | 71.8 | | |
| CFA/IFA | | | | 15.9 | | |
| IL-12 | | | | 8.4 | | |
| GM-CSF | | | | 7.3 | | |
| MPL™ SE | 190.1 | 51.5 | 319.0 | 187.3 | | |
| MPL™ SE + IL-12 | 18.0 | 15.6 | 42.0 | 83.4 | | 12.7 |
| MPL™ SE + GM-CSF | 62.2 | 20.2 | 39.2 | 134.7 | | |
| SE | 13.3 | | | 54.6 | | |

Experiment 2

Immunization of Balb/c Mice with an HIV Peptide and Various Adjuvants

Example 8

Materials and Methods

Animals

Female Balb/c mice, aged 7-9 weeks, were used according to Example 1 above.

Peptides

The HIV-1-MN peptide T1SP10MN(A) described in Example 1 was used. The peptide was rehydrated in saline to a concentration of 1 mg/ml.

Adjuvants

The adjuvants used were as described in Example 1, except that in some instances the MPL™ was retained as an aqueous formulation instead of using the stable emulsion form.

Immunizations

Mice were immunized subcutaneously in the rump, in a total volume of 0.2 ml equally divided on each side of the tail. Immunizations were administered on days 0 and 21 with 25 µg of the HIV peptide, together with the indicated amount of adjuvant(s). Mice receiving CFA/IFA received CFA on day 0 and IFA on day 21. Dilutions and mixing were as described in Example 1.

Sample Collections

Sample collections from animals were carried out in accordance with the protocol of Example 1 one day prior to each immunization and 14 days after the second immunization.

Cell Preparations

Cell preparations were generated and handled in accordance with the protocol of Example 1.

Enzyme-Linked Immunosorbent Assays

ELISAs were carried out in accordance with the protocol of Example 1.

HIV-1$_{MN}$ Neutralization Assays

Neutralization assays were again performed at Duke University in accordance with the protocol of Example 1.

Example 9

Reciprocal Anti-T1SP10MN(A) (−Cys) IgG Endpoint Titers

Reciprocal anti-peptide IgG endpoint titers were measured from either geometric means from individual mice (GMT) or from pooled serum (n=5 Balb/c), obtained 14 days after the second immunization. IgG1 and IgG2a subclass endpoint titers were also measured from pooled serum. For recipients of Freund's adjuvants, mice were primed with 25 µg peptide emulsified in CFA, and boosted with IFA. MPL™ SE was provided as an emulsion containing 1% squalene oil and 50 µg MPL™ per dose. Aqueous MPL™ was delivered at 50 µg per dose. Recombinant murine IL-12 was delivered at 40 ng/mouse. Recombinant murine GM-CSF was delivered at 10 µg/mouse. The results are given in Table 7.

TABLE 7

Reciprocal anti-T1SP10MN(A) (−Cys) IgG endpoint titers

| | Endpoint Titers | | | |
|---|---|---|---|---|
| Adjuvant µg/dose | IgG (pool) | IgG (GMT) | IgG1 (pool) | IgG2a (pool) |
| None | <1000 | 720 | <1000 | <1000 |
| CFA/IFA | 72,387 | 135,740 | 126,433 | 9,023 |
| MPL ™ SE | 183,802 | 197,808 | 162,480 | 98,342 |
| SE | 2,426 | 6,029 | 1,859 | <1000 |
| MPL ™ SE + GM-CSF | 148,139 | 133,171 | 103,298 | 50,415 |
| MPL ™ SE + rIL-12 | 182,852 | 611,076 | 6,610 | 111,662 |
| GM-CSF | 27,333 | 1,756 | 14,538 | 4,864 |
| rIL-12 | <1000 | 500 | <1000 | <1000 |
| MPL ™ | 219,705 | 241,918 | 134,428 | 7,127 |
| MPL ™ + GM-CSF | 946,695 | 1,101,449 | 545,444 | 12,291 |
| MPL ™ + rIL-12 | 377,972 | 2,378,702 | 204,334 | 12,795 |

Example 10

Reciprocal Anti-T1SP10MN(A) (−Cys) IgG Endpoint Subclass Titers

HIV peptide-specific vaginal lavage endpoint reciprocal endpoint IgG and IgA antibody titers were measured from pooled serum (n=5 Balb/c) 15 days after secondary immunization. Mice were immunized as in Example 9. MPL™ SE was provided as an emulsion containing 1% squalene oil and 50 µg MPL™ per dose. Aqueous MPL™ was delivered at 50 µg per dose. Recombinant murine IL-12 was delivered at 40 ng/mouse. Recombinant murine GM-CSF was delivered at 10 µg/mouse. The results are given in Table 8.

TABLE 8

Reciprocal anti-T1SP10MN(A) (−Cys) IgG and IgA endpoint titers

| | Endpoint Titers | |
|---|---|---|
| Adjuvants | IgG | IgA |
| None | <10 | <10 |
| CFA/IFA | <10 | <10 |
| MPL ™ SE (1%) | 32 | <10 |
| SE | <10 | <10 |
| MPL ™ SE (1%) + GM-CSF | 129 | <10 |
| MPL ™ SE (1%) + IL-12 | 40 | <10 |
| GM-CSF | 26 | <10 |
| rIL-12 | <10 | <10 |
| MPL ™ | <10 | <10 |
| MPL ™ + GM-CSF | <10 | <10 |
| MPL ™ + IL-12 | 260 | 197 |

Example 11

Spleen Cell Proliferation

Spleen cell proliferation in response to in vitro stimulation with T1SP10MN(A) (−Cys) and various adjuvant formulations (the same as in Example 10) was measured. Cells were cultured for a total of 96 hours. $^3$H-thymidine was added to cultures for the last 18 hours. Data are presented as a proliferation index normalized to cells stimulated in culture with ConA ([mean cpm Antigen/mean cpm ConA]−[mean cpm medium/mean cpm ConA])×100. As a result, cells cultured in medium have a background proliferation of 0. The results are given in Table 9. Proliferation values less than cells grown in culture unstimulated are in parentheses.

TABLE 9

Spleen cell proliferation

| | Antigen | | | | |
|---|---|---|---|---|---|
| Adjuvant | HIV Peptide 10 µg/ml | HIV Peptide 3.3 µg/ml | HIV Peptide 1.1 µg/ml | Con A 5 µg/ml | Lysozyme 10 µg/ml |
| None | 0.1 | 0.2 | 0.1 | 98.3 | 0.4 |
| CFA/IFA | 2.0 | 0.8 | 0.4 | 98.0 | 0.9 |
| MPL ™ SE | 0.7 | 0.4 | (0.2) | 99.2 | 0.4 |
| SE | 0.5 | 0.3 | 0.1 | 99.0 | 0.4 |
| MPL ™ SE + GM-CSF | 4.3 | 2.7 | 2.3 | 99.1 | 0.8 |
| MPL ™ SE + IL-12 | 6.6 | 4.9 | (1.3) | 83.8 | 17.4 |
| GM-CSF | 6.8 | 2.7 | 1.6 | 99.0 | 0.1 |
| IL-12 | 0.2 | 0.2 | 0.5 | 99.1 | 0.2 |
| MPL ™ | 1.0 | 1.4 | 0.5 | 99.2 | 0.4 |
| MPL ™ + GM-CSF | 27.5 | 19.2 | 13.3 | 97.5 | 0.5 |
| MPL ™ + IL-12 | 2.3 | 1.5 | 1.3 | 99.4 | (0.0) |

Example 12

Secretion of IL-4 by Spleen Cells

Interleukin-4 secreted into culture by spleen cells stimulated with T1SP10MN(A) (−Cys) was measured. Cells were cultured for a total of 96 hours. Cell culture supernatants were analyzed for IL-4 by ELISA. All values were after subtraction from those determined from supernatants of cells stimulated with 10 µg of an irrelevant protein (lysozyme). The results are given in Table 10 in pg/ml. Results which were below the limit of detection, after subtraction from stimulation induced with lysozyme are indicated as "bd". The adjuvants were 40 ng IL-12, 10 µg GM-CSF and 50 µg MPL™.

TABLE 10

Secretion of IL-4 by Spleen Cells

| Adjuvant | Antigen | | | |
|---|---|---|---|---|
| | HIV Peptide 10 µg/ml | HIV Peptide 3.3 µg/ml | HIV Peptide 1.1 µg/ml | Con A 5 µg/ml |
| None | bd | bd | bd | 336 |
| CFA/IFA | bd | bd | bd | 117 |
| MPL ™ SE | bd | bd | bd | 187 |
| SE | bd | bd | bd | 450 |
| MPL ™ SE + GM-CSF | 40 | 42 | 24 | 214 |
| MPL ™ SE + IL-12 | 5 | bd | bd | 266 |
| GM-CSF | bd | 9 | 36 | 226 |
| IL-12 | bd | bd | 15 | 411 |
| MPL ™ | 5 | bd | 17 | 286 |
| MPL ™ + GM-CSF | bd | bd | bd | 241 |
| MPL ™ + IL-12 | bd | bd | bd | 665 |

Example 13

Secretion of Interferon-Gamma by Spleen Cells

Interferon-gamma secreted into culture by spleen cells stimulated with T1SP10MN(A) (–Cys) was measured. Cells were cultured for a total of 96 hours. Cell culture supernatants were analyzed for interferon-gamma by ELISA. All values were after subtraction from those determined from supernatants of cells stimulated with 10 µg of lysozyme. The results are given in Table 11 in units/ml. Results which were below the limit of detection, after subtraction from stimulation induced with lysozyme are indicated as "bd". The adjuvants were the same as those in Example 12.

TABLE 11

Secretion of Interferon-gamma by Spleen Cells

| Adjuvant | Antigen | | | |
|---|---|---|---|---|
| | HIV Peptide 10 µg/ml | HIV Peptide 3.3 µg/ml | HIV Peptide 1.1 µg/ml | Con A 5 µg/ml |
| None | bd | bd | 1 | 189 |
| CFA/IFA | bd | bd | 3 | 193 |
| MPL ™ SE | 2 | bd | bd | 170 |
| SE | bd | bd | bd | 130 |
| MPL ™ SE + GM-CSF | 12 | 3 | 5 | 138 |
| MPL ™ SE + IL-12 | 23 | 8 | 9 | 168 |
| GM-CSF | 2 | 3 | 4 | 167 |
| IL-12 | 4 | 2 | 41 | 179 |
| MPL ™ | 5 | bd | bd | 203 |
| MPL ™ + GM-CSF | bd | 20 | 19 | 31 |
| MPL ™ + IL-12 | 10 | 4 | 3 | 51 |

Experiment 3

Immunization of Swiss-Webster Mice with an HIV Peptide and Various Adjuvants

The protocols of Experiment 2 were followed, with Swiss-Webster mice used instead of Balb/c mice. Only reciprocal anti-peptide IgG endpoint titers and vaginal lavage endpoint reciprocal endpoint IgG and IgA antibody titers were measured in this experiment.

Example 14

Reciprocal anti-HIV Peptide IgG Endpoint Titers

Reciprocal anti-T1SP10MN(A) (–Cys) IgG endpoint titers were measured from geometric means from individual Swiss-Webster mice (GMT), obtained 14 days after the second immunization. IgG1 and IgG2a subclass endpoint titers were also measured from pooled serum. For recipients of Freund's adjuvants, mice were primed with peptide emulsified in CFA, and boosted with IFA. MPL™ SE was provided as an emulsion containing 1% squalene oil and 50 µg MPL™ per dose. Aqueous MPL™ was delivered at 50 µg per dose. Recombinant murine IL-12 was delivered at 40 ng/mouse. Recombinant murine GM-CSF was delivered at 10 µg/mouse. The results are given in Table 12.

TABLE 12

Reciprocal anti-HIV peptide IgG endpoint titers

| | Endpoint Titers | | |
|---|---|---|---|
| Adjuvant | IgG (GMT) | IgG1 (pool) | IgG2a (pool) |
| None | 500 | <1000 | <1000 |
| CFA/IFA | 9,038 | 62,358 | 54,053 |
| MPL ™ SE | 15,831 | 3,835 | 8,872 |
| SE | 625 | <1000 | <1000 |
| MPL ™ SE + GM-CSF | 1,374 | <1000 | 1,328 |
| MPL ™ SE + rIL-12 | 6,142 | <1000 | 2,170 |
| GM-CSF | 500 | <1000 | <1000 |
| rIL-12 | 500 | <1000 | <1000 |
| MPL ™ | 1,960 | <1000 | <1000 |
| MPL ™ + GM-CSF | 58,211 | 35,724 | 37,959 |
| MPL ™ + rIL-12 | 5,489 | 8,535 | 17,769 |

Example 15

Reciprocal Anti-HIV Peptide IgG Endpoint Subclass Titers

HIV peptide-specific vaginal lavage endpoint reciprocal endpoint IgG and IgA antibody titers were measured from pooled serum (n=5 Swiss-Webster) 15 days after secondary immunization. Mice were immunized as in Example 14. MPL™ SE was provided as an emulsion containing 1% squalene oil and 50 µg MPL™ per dose. Aqueous MPL™ was delivered at 50 µg per dose. Recombinant murine IL-12 was delivered at 40 ng/mouse. Recombinant murine GM-CSF was delivered at 10 µg/mouse. The results are given in Table 13.

TABLE 13

Reciprocal anti-HIV peptide IgG and IgA endpoint titers

| Adjuvants | Endpoint Titers | |
|---|---|---|
| | IgG | IgA |
| None | <10 | <10 |
| CFA/IFA | 118 | <10 |
| MPL ™ SE (1%) | <10 | <10 |
| SE | <10 | <10 |
| MPL ™ SE (1%) + GM-CSF | <10 | <10 |
| MPL ™ SE (1%) + IL-12 | <10 | <10 |
| GM-CSF | <10 | <10 |
| rIL-12 | <10 | <10 |
| MPL ™ | <10 | <10 |
| MPL ™ + GM-CSF | 25 | <10 |
| MPL ™ + IL-12 | <10 | <10 |

Experiment 4

Immunization of Balb/c Mice with an HIV Peptide and Various Adjuvants

The protocols of Experiment 2 were followed, except that mice were immunized on days 0 and 28, and bled for serological evaluation on days 0, 27 and 41. CFA/IFA was formulated with CFA at day 0, IFA at day 28. MPL™ SE was formulated with 50 µg MPL™ and 2% SE, while 50 ng IL-12 and 10 µg GM-CSF were used.

Example 16

Reciprocal Anti-HIV Peptide IgG Endpoint Titers

Reciprocal anti-T1SP10MN(A) (–Cys) IgG endpoint titers were measured from individual mice and their geometric means (n=5 Balb/c) 41 days after initial immunization, 13 days after secondary immunization. The results are given in Table 14. The day zero individual titers were all less than 50. The notation "[no data]" means the animal died prior to the completion of the protocol. "SD" means standard deviation.

Example 17

Reciprocal Anti-HIV Peptide IgG Endpoint Subclass Titers

Reciprocal endpoint anti-peptide IgG subclass titers were measured from pooled serum (n=5 Balb/c) 41 days after initial immunization, 13 days after secondary immunization. The results are given in Table 15.

TABLE 15

Reciprocal anti-T1SP10MN(A) (–Cys) IgG endpoint subclass titers

| Adjuvants | Endpoint Titers | | |
|---|---|---|---|
| | IgG1 | IgG2a | IgG2b |
| CFA/IFA | 359,238 | 122,107 | 155,877 |
| IL-12 | <100 | <100 | <100 |
| GM-CSF | 5,514 | <100 | <100 |
| SE | 5,011 | <100 | <100 |
| SE + IL-12 | 7,331 | <100 | <100 |
| SE + GM-CSF | 67,111 | <100 | <100 |
| MPL ™ | 33,544 | 212 | <100 |
| MPL ™ + IL-12 | 608,163 | 6,019 | <100 |
| MPL ™ + GM-CSF | 114,959 | 8,000 | <100 |
| MPL ™ SE | 142,404 | 29,141 | 1,564 |
| MPL ™ SE + IL-12 | 164,866 | 34,439 | 558 |
| MPL ™ SE + GM-CSF | 274,241 | 33,843 | 29,965 |

Example 18

Vaginal Lavage IgG and IgA Anti-HIV Peptide Antibody Titers

Vaginal IgG and IgA anti-peptide antibody titers were measured from lavage 41 days after initial immunization, 13 days after secondary immunization. The results are given in Table 16.

TABLE 14

Individual and Geometric Mean IgG Serum Titers Specific for T1SP10MN(A) (–Cys)

| Adjuvant | Mouse #1 | Mouse #2 | Mouse #3 | Mouse #4 | Mouse #5 | GMT | SD |
|---|---|---|---|---|---|---|---|
| CFA/IFA | 2,806,160 | 4,856,380 | 148,038 | 172,947 | 972,484 | 805,599 | 2,025,740 |
| IL-12 | 594 | 50 | 50 | 50 | 50 | 82 | 243 |
| GM-CSF | 50 | 50 | 50 | 50 | 50 | 50 | 0 |
| SE | 11,469 | [no data] | 5,519 | 12,620 | 50 | 2,514 | 5,813 |
| SE + IL-12 | 38,042 | 8,030 | 35,081 | 50 | 37,932 | 7,271 | 18,320 |
| SE + GM-CSF | 485,985 | 223,518 | 63,377 | 38,050 | 1,857,860 | 217,494 | 761,374 |
| MPL ™ | 50 | 151,846 | 249,054 | 436,378 | 1,245,470 | 63,452 | 490,091 |
| MPL ™ + IL-12 | 1,855,170 | 1,117,800 | 1,255,290 | 692,219 | 7,001,540 | 1,660,297 | 2,614,417 |
| MPL ™ + GM-CSF | 115,527 | 1,049,310 | 301,636 | 316,223 | 736,959 | 958,568 | 380,380 |
| MPL ™SE | 904,947 | 5,805,010 | 291,382 | 346,835 | 354,449 | 716,000 | 2,396,968 |
| MPL ™SE + IL-12 | 244,171 | 8,545,550 | 455,380 | 377,697 | 1,095,650 | 829,707 | 3,593,727 |
| MPL ™SE + GM-CSF | 3,016,000 | 724,940 | 1,718,590 | 1,483,990 | 28,259 | 691,033 | 1,124,414 |

TABLE 16

Vaginal Lavage IgG and IgA
anti-T1SP10MN(A) (–Cys) Antibody Titers

| Adjuvant | IgG | IgA |
|---|---|---|
| CFA/IFA | 464 | 13 |
| IL-12 | <10 | <10 |
| GM-CSF | <10 | <10 |
| SE | <10 | <10 |
| SE + IL-12 | <10 | <10 |
| SE + GM-CSF | 32 | 14 |
| MPL ™ | 12 | <10 |
| MPL ™ + IL-12 | 643 | 44 |
| MPL ™ + GM-CSF | 211 | 65 |
| MPL ™ SE | 153 | 16 |
| MPL ™ SE + IL-12 | 88 | 30 |
| MPL ™ SE + GM-CSF | 190 | 53 |

Example 19

Spleen Cell Proliferation

Proliferation of spleen cells from mice immunized with T1SP10MN(A) (–Cys) and various adjuvant formulations was measured. Spleen cells were stimulated in vitro for four days with 3.3 µg/ml T1SP10MN(A) (–Cys). The results are shown in FIG. 4 as the change in the incorporation of labeled thymidine as a result of in vitro stimulation with 3.3 µg/ml T1SP10MN(A) (–Cys) over the incorporation in the absence of stimulation (delta cpm).

Experiment 5

Immunization of Balb/c Mice with an HIV Peptide and Various Adjuvants

The protocols of Experiment 2 were followed, except that mice were immunized subcutaneously on days 0 and 22, and bled for serological evaluation on day 42. MPL™ SE was formulated with 50 µg MPL™ and 1% SE, while 10 µg GM-CSF were used.

Example 20

Reciprocal Anti-HIV Peptide IgG Endpoint Titers

Reciprocal anti-peptide endpoint IgG subclass titers were measured from pooled serum (n=5 Balb/c) 42 days after initial immunization, 13 days after secondary immunization. Geometric means with standard deviation for IgG were also measured. The results are given in Table 17.

TABLE 17

Reciprocal anti-T1SP10MN(A) (–Cys) IgG Endpoint Titers

| Adjuvant | IgG | IgG1 | IgG2a | IgG2b | IgG GMT | SD |
|---|---|---|---|---|---|---|
| Non | <1000 | <1000 | <1000 | <1000 | <1000 | — |
| CFA/IFA | 390,931 | 144,564 | 33,137 | 13,134 | 741,966 | 834,567 |
| GM-CSF | 11,639 | 3,815 | <1000 | <1000 | 5,133 | 32,762 |
| SE | <1000 | <1000 | <1000 | <1000 | <1000 | — |
| SE + GM-CSF | 84,965 | 55,998 | <1000 | <1000 | 28,247 | 165,628 |
| MPL ™ | 2,635,118 | 1,314,771 | 9,688 | 13,716 | 2,032,441 | 5,638,450 |
| MPL ™ + GM-CSF | 835,218 | 322,441 | | | | |
| MPL ™ SE | 1,577,357 | 642,436 | | | | |
| MPL ™ SE + GM-CSF | 6,598,573 | 1,212,160 | 238,440 | 214,570 | 6,148,920 | 2,925,687 |

Experiment 6

Immunization of Balb/c Mice with an HIV Peptide and Various Adjuvants

The protocols of Experiment 2 were followed, except that the HIV peptide contained a cysteine at amino acid position 17, and the mice (n=3 Balb/c) were immunized subcutaneously on days 0 and 21, and bled for serological evaluation on days −1 (the day before first immunization), 13, 20 and 28. MPL™ SE was formulated with 50 µg MPL™ and 1% SE, while 10 µg GM-CSF were used. The HIV peptide T1SP10MN(A) (+Cys) (26) contains a cysteine at amino acid position 17 and is 40 residues long. T1SP10MN(A) (+Cys) was purchased from Genosys Biotechnologies (The Woodlands, Tex.).

Example 21

Reciprocal Anti-T1SP10MN(A) IgG Endpoint Titers

Reciprocal anti-T1SP10MN(A) IgG endpoint titers were measured from individual mice and their geometric means (n=3 Balb/c) 28 days after initial immunization. The results are given in Table 18.

TABLE 18

Effect of MPL ™ SE + GM-CSF on the IgG Response to HIV Peptide (+Cys)

| Adjuvant | IgG | GMT | IgG1 | GMT | IgG2a | GMT | IgG2b | GMT |
|---|---|---|---|---|---|---|---|---|
| MPL ™ SE + | 14,275,585 | 8,942,480 | 2,097,104 | 1,437,319 | 251,235 | 239,615 | 210,746 | 210,178 |
| GM-CSF | 13,618,523 |  | 2,484,849 |  | 225,253 |  | 296,429 |  |
|  | 3,678,324 |  | 569,823 |  | 243,103 |  | 148,621 |  |
| MPL ™ SE | 1,913,110 | 5,206,349 | 644,377 | 990,194 | 22,557 | 114,913 | 23,141 | 70,632 |
|  | 11,405,649 |  | 1,937,492 |  | 152,430 |  | 127,600 |  |
|  | 6,467,553 |  | 777,643 |  | 441,326 |  | 119,338 |  |
| MPL ™ | 91,728 | 350,486 | 23,249 | 84,978 | 500 | 2,859 | 500 | 2,906 |
|  | 529,663 |  | 155,199 |  | 1,628 |  | 1,102 |  |
|  | 886,156 |  | 170,071 |  | 28,722 |  | 44,531 |  |
| None | <500 | — | <500 | — | <500 | — | <500 | — |
|  | <500 |  | <500 |  | <500 |  | <500 |  |
|  | <500 |  | <500 |  | <500 |  | <500 |  |

Experiment 7

Immunization of Balb/c Mice with an HIV Peptide and Various Adjuvants

The protocols of Experiment 6 were followed, except that mice (n=3 Balb/c) were immunized subcutaneously on days 0 and 32, and bled for serological evaluation on day 38. MPL™ SE was formulated with 50 µg MPL™ and 1% SE, while 10 µg GM-CSF were used.

Example 22

Reciprocal Anti-HIV Peptide IgG Endpoint Titers

Reciprocal anti-T1SP10MN(A) (+Cys) IgG endpoint titers were measured from individual mice and their geometric means (n=3 Balb/c) 38 days after initial immunization. The results are given in Table 19.

was assessed. MPL™ SE was formulated with 50 µg MPL™ in 1% SE, with or without 10 µg GM-CSF, plus 50 µg T1SP10MN(A) (+Cys).

Example 23

CTL Analysis in Balb/c Mice

For CTL analysis, spleen cells were removed from immunized mice 14 days after primary, and seven days after secondary immunization. A protocol previously described (34) was essentially followed. Briefly, erythrocyte-depleted spleen cells from three mice per group were pooled. Spleen effector cells ($4 \times 10^6$/ml) were restimulated in 24 well culture plates in a volume of 1.5-2 ml for seven days with 1 µg/ml of either the "MN", or the "IIIB" 10mer CTL epitope peptides. Both CTL epitopes were restricted to H-$2D^d$. Cultures were supplemented with 10 U/ml recombinant murine IL-2 (Biosource) for the last five days of culture. For analysis of cyto-

TABLE 19

Effect of MPL ™ SE + GM-CSF on the IgG Response to HIV Peptide (+Cys)

| Adjuvant | IgG | GMT | IgG1 | GMT | IgG2a | GMT | IgG2b | GMT |
|---|---|---|---|---|---|---|---|---|
| MPL ™ SE + | 4,144,648 | 4,782,117 | 922,507 | 1,090,760 | 115,290 | 328,097 | 74,130 | 64,521 |
| GM-CSF | 5,055,375 | +/− | 985,180 | +/− | 629,615 | +/− | 76,257 | +/− |
|  | 5,219,387 | 472,745 | 1,427,916 | 224,940 | 486,563 | 216,753 | 47,515 | 13,077 |
| MPL ™ SE | 736,325 | 559,033 | 288,659 | 293,160 | 58,506 | 103,260 | 33,047 | 27,180 |
|  | 696,393 | +/− | 809,341 | +/− | 244,559 | +/− | 46,703 | +/− |
|  | 340,712 | 177,831 | 107,844 | 297,378 | 76,951 | 83,698 | 13,010 | 13,837 |
| MPL ™ + | 444,774 | 1,367,343 | 146,146 | 611,040 | 3,342 | 8,546 | 2,155 | 7,067 |
| GM-CSF | 3,993,897 | +/− | 3,568,062 | +/− | 17,469 | +/− | 14,130 | +/− |
|  | 1,439,116 | 1,494,876 | 437,511 | 1,549,005 | 10,691 | 5,769 | 11,590 | 5,152 |
| MPL ™ | 404,755 | 442,259 | 148,818 | 115,544 | 11,874 | 3,429 | 9,685 | 4,980 |
|  | 446,952 | +/− | 90,380 | +/− | 1,674 | +/− | 3,605 | +/− |
|  | 478,163 | 30,080 | 114,686 | 23,969 | 2,028 | 4,727 | 3,538 | 2,882 |
| SE | <1,000 | <1,000 | <1,000 | <1,000 | <1,000 | <1,000 | <1,000 | <1,000 |
|  | <1,000 |  | <1,000 |  | <1,000 |  | <1,000 |  |
|  | 1,214 |  | <1,000 |  | <1,000 |  | <1,000 |  |
| None | <1,000 | <1,000 | <1,000 | <1,000 | <1,000 | <1,000 | <1,000 | <1,000 |
|  | <1,000 |  | <1,000 |  | <1,000 |  | <1,000 |  |
|  | <1,000 |  | <1,000 |  | <1,000 |  | <1,000 |  |

Experiment 8

CTL Analysis in Balb/c Mice

The protocols of Experiment 6 were followed regarding immunization of mice. The CTL activity of spleen cells isolated from mice seven days after secondary immunization toxic activity, P815 cells were labeled with $Cr^{51}$ and pulsed with 5 µg/ml peptide (IIIB or MN) for four hours, and added to cultured splenic effector cells. Three-fold dilutions of effector to target cell ratios were used, from 100:1 through 3.7:1. Percent CTL activity was calculated as the percentage of chromium release using ((specific chromium release−spontaneous chromium release)/(maximal chromium release−spontaneous chromium release))×100. Chromium release was assessed after a six hour incubation period. The average spontaneous release of chromium was always less than 15% of maximal release. The results of data from day 28 are shown in FIG. 5.

Experiment 9

Immunization of Rhesus Macaques with Various SIV Peptides and Adjuvants

The MPL™ SE and GM-CSF adjuvant formulation was tested in Rhesus macaques (*Macaca mulatta*) for its ability to induce antigen-specific CTL. In this experiment, the adjuvant formulation was tested with a trivalent peptide immunogen consisting of three separate Mamu A*01 restricted CTL epitopes (one each from gag, pol, and env), each synthesized chemically with or without a promiscuous T-helper epitope from SIV env at the laboratory of Dr. Barton Haynes, Duke University.

The peptides containing a Mamu A*01 restricted CTL epitope were as follows:

Cys Thr Pro Tyr Asp Ile Asn Gln Met (SEQ ID NO:3) (gag) Ser Thr Pro Pro Leu Val Arg Leu Val (SEQ ID NO:4) (pol) Tyr Ala Pro Pro Ile Ser Gly Gln Ile (SEQ ID NO:5) (env)

Each of these CTL-containing epitopes was also linked to the T-helper epitope having the following sequence:

Glu Leu Tyr Lys Tyr Lys Val Val Lys Ile Glu Pro Leu Gly Val Ala Pro Thr Lys Ala (SEQ ID NO:6)

Thus, the three multiepitope peptides had the following sequences:

Glu Leu Tyr Lys Tyr Lys Val Val Lys Ile Glu Pro Leu Gly Val Ala Pro Thr Lys Ala Cys Thr Pro Tyr Asp Ile Asn Gln Met (SEQ ID NO:7)

Glu Leu Tyr Lys Tyr Lys Val Val Lys Ile Glu Pro Leu Gly Val Ala Pro Thr Lys Ala Ser Thr Pro Pro Leu Val Arg Leu Val (SEQ ID NO:8)

Glu Leu Tyr Lys Tyr Lys Val Val Lys Ile Glu Pro Leu Gly Val Ala Pro Thr Lys Ala Tyr Ala Pro Pro Ile Ser Gly Gln Ile (SEQ ID NO:9)

CTL analysis was conducted by Mamu A*01 restricted tetramer staining analysis at the laboratory of Dr. Norman Letvin, Harvard Medical School.

Animals, Doses and Immunogens:

Rhesus macaques expressing the HLA-A homologue molecule Mamu A*01 and the subtype DRβ0201 were identified by PCR and housed at the colony at New Iberia, La.

The study included three groups of two juvenile Rhesus macaques (*Macaca mulatta*) each described in Table 20. Group 1 consisted of two Mamu A*01 positive, DRβ0201 negative animals Rh 73 and Rh 80. These animals were administered the trivalent Mamu A*01 restricted SIV gag, env and pol CTL epitope peptides (short peptide cocktail), together with MPL™ SE and GM-CSF. Group 2 consisted of two Mamu A*01 positive, DRβ0201 positive macaques which received the Th/SIVCTL gag, pol and env epitope peptides (long peptide cocktail), together with MPL™ SE and GM-CSF. Group 3 comprised of two Mamu A*01 negative, DRβ0201 positive animals inoculated with the Th/SIVCTL gag, pol and env peptides (long peptide cocktail). Table 20 sets forth the groups by HLA type and peptide immunogens used.

TABLE 20

Animals, Doses and Immunogens

| Group | Animal # | HLA type | Peptide Immunogens |
|---|---|---|---|
| 1 | Rh 73, Rh 80 | Mamu A*01 + DR*β0201 − | CTL/SIV gag p11C (SEQ ID NO:3) CTL/SIV pol p68A (SEQ ID NO:4) CTL/SIV env p41A (SEQ ID NO:5) 0.75 mg of each peptide |
| 2 | Rh 55, Rh 142 | Mamu A*01 + DR*β0201 + | Th1/CTL/SIV gag p11C (SEQ ID NO:7) Th1/CTL/SIV pol p68A (SEQ ID NO:8) Th1/CTL/SIV env p41A (SEQ ID NO:9) 2.4 mg of each peptide |
| 3 | Rh 41, Rh 47 | Mamu A*01 − DR*β0201 + | Th1/CTL/SIV gag p11C (SEQ ID NO:7) Th1/CTL/SIV pol p68A (SEQ ID NO:8) Th1/CTL/SIV env p41A (SEQ ID NO:9) 2.4 mg of each peptide |

All groups were immunized subcutaneously with 1 ml of the respective peptide cocktail formulated in 50 μg MPL™ SE in 1% oil and 250 μg human GM-CSF at 0, 4, and 8 weeks. The dose of MPL™ SE was increased to 125 μg in 1% oil for the 18 week immunization. For all groups, 2.4 mg of each of the long peptides and 0.75 mg of each of the short peptides were dissolved in 900 μl distilled, deionized water. The peptide solution was then used for reconstitution of the human GM-CSF, and 100 μl of the MPL™ SE formulation was added.

Example 24

CTL Analysis in Rhesus Macaques

Animals were bled every two weeks and heparinized blood analyzed for Mamu A*01 restricted CTL by tetramer staining on fresh and cultured peripheral blood mononuclear cells (PBMC) (50). PBMC were stimulated with either p11c, p68A, p41A or p46 on day 0 and then cultured in the presence of IL-2 and analyzed on day 11. Standard $^{51}$Cr release assay was also carried out on cultured PBMC (50).

A tetramer assay was carried out as follows: Epitope peptides p11c from gag, p68A from pol or p68A from pol or p41A from env were incubated with purified biotinylated Mamu A*01 in the presence of β2 microglobulin, then attached to avidin and conjugated to PE (phycoerythrin). This tetramer was then used for staining macaque CD8+ cells with T cell receptors that recognize the p11C, p68A or p41A epitopes. A different DRβ0201 tetramer folded around the dominant env p46 epitope allowed for staining of CD4+ cells that specifically recognized the p46 Th epitope. The results are shown in Tables 21-24.

TABLE 21

Percent P11c/SIVgag tetramer positive CD8+ cells

| | Weeks | 0 | 2 | 4 | 6 | 8 | 9 | 10 | 14 |
|---|---|---|---|---|---|---|---|---|---|
| Group 1 | Rh 73 | 0.1 | 3.9 | 5.1 | 4.2 | 2.7 | 2.6 | 0.1 | 2.7 |
| | Rh 80 | 0.1 | 0.4 | 0.1 | 0.6 | 0.2 | 0.2 | 1.4 | 0.2 |
| Group 2 | Rh 55 | 0.1 | 3.1 | 4.5 | 5.9 | 4.0 | 4.0 | 4.1 | 2.7 |
| | Rh 142 | 0.2 | 4.7 | 2.5 | 5.4 | 3.9 | 3.9 | 2.5 | 4.1 |
| Group 3 | Rh 41 | 0 | 0.2 | 0.2 | 0.3 | 0.2 | 0.2 | 0.1 | 0.1 |
| | Rh 47 | 0.1 | 0.3 | 0.1 | 0.2 | 0.1 | 0.1 | 0.0 | 0.1 |

TABLE 22

Percent p68A/SIV CTL pol tetramer positive CD8+ cells

| | Weeks | 0 | 2 | 4 | 6 | 8 | 9 | 10 | 14 |
|---|---|---|---|---|---|---|---|---|---|
| Group 1 | Rh 73 | 0.1 | 0.4 | 0.1 | 10.1 | 2.5 | 0.5 | 1.8 | 1.5 |
| | Rh 80 | 0.2 | 0.2 | 0.6 | 2.3 | 0.5 | 0.1 | 0.1 | 0.1 |
| Group 2 | Rh 55 | 0.1 | 1.1 | 1.1 | 5.5 | 5.6 | 1.5 | 11.7 | 6.4 |
| | Rh 142 | 0.2 | 0.6 | 0.2 | 1.0 | 1.8 | 0.3 | 2.3 | 1.2 |
| Group 3 | Rh 41 | 0.1 | 0.2 | 0.1 | 0.3 | 0.1 | 0.1 | 0.1 | 0.3 |
| | Rh 47 | 0.1 | 0.1 | 0.1 | 0.3 | 0.3 | 0.1 | 0.1 | |

TABLE 23

Percent P41A/SIV env tetramer positive CD8+ cells

| | Weeks | 0 | 2 | 4 | 6 | 8 | 9 | 10 | 14 |
|---|---|---|---|---|---|---|---|---|---|
| Group 1 | Rh 73 | 0.8 | 3.5 | 2.5 | 2.0 | 3.5 | 1.7 | 1.5 | 1.5 |
| | Rh 80 | 0.2 | 0.2 | 3.4 | 0.5 | 0.1 | 0.0 | 0.2 | 0.2 |
| Group 2 | Rh 55 | 0.2 | 1.1 | 0.4 | 0.6 | 0.4 | 0.2 | 0.1 | 0.6 |
| | Rh 142 | 0.3 | 0.5 | 0.4 | 0.6 | 0.3 | 0.3 | 0.2 | 0.4 |
| Group 3 | Rh 41 | 0 | 0.2 | 0.1 | 0.3 | 0.0 | 0.0 | 0.2 | 0.2 |
| | Rh 47 | 0.1 | 0.2 | 0.1 | 0.2 | 0.2 | 0.1 | 0.0 | 0.2 |

TABLE 24

Percent p46/SIV T helper DRβ0201 tetramer positive CD4+ cells

| | Weeks | 0 | 2 | 4 | 6 | 8 | 9 | 10 | 14 |
|---|---|---|---|---|---|---|---|---|---|
| Group 1 | Rh 73 | | | 0.2 | 0.0 | 0.0 | 0.0 | 0.0 | 0.0 |
| | Rh 80 | | | 0.2 | 0.0 | 0.0 | 0.1 | 0.0 | 0.0 |
| Group 2 | Rh 55 | | | 0.2 | 0.5 | 0.7 | 0.4 | 0.3 | 0.3 |
| | Rh 142 | | | 0.2 | 0.9 | 0.6 | 1.0 | 0.6 | 0.5 |
| Group 3 | Rh 41 | | | | | 0.6 | 0.4 | 0.3 | 0.3 |
| | Rh 47 | | | | | 1.2 | 0.8 | 1.6 | 1.2 |

Experiment 10

Immunization of Swiss-Webster Mice with a *Neisseria gonorrhoeae* Porin B Protein and Various Adjuvants Outbred Swiss-Webster mice were divided into five groups of ten mice each. Each group received 1 µg of recombinant Porin B protein (from strain FA1090 with 16 amino acids at the amino-terminus from a phage, followed by the mature form of the Porin B protein). The first group did not receive an adjuvant; the second group received 50 µg of MPL™; the third group received MPL™ plus 5 µg GM-CSF; the fourth group received 25 µg MPL™ SE; the fifth group received MPL™ SE plus 5 µg GM-CSF. Mice were immunized subcutaneously in the rump with a total volume of 0.2 ml, divided equally into each of two sites at the base of the tail/rump. Immunizations were administered at week 0 and week 4.

Example 25

Reciprocal Anti-Porin B Protein IgG Endpoint Subclass Titers

Mice were bled the day prior to each immunization, and at 13 days after the final immunization. Serum was analyzed from pools from mice within groups. Reciprocal endpoint anti-Porin B protein IgG subclass titers were measured from pooled serum (n=10 Swiss-Webster) by vaginal lavage at week 3 and at week 6. The results are given in Table 25. All day 0 pre-immunization titers were less than 50.

TABLE 25

Reciprocal anti-Porin B Protein IgG Endpoint Sublass Titers

| | Week 3 | | | Week 6 | | |
|---|---|---|---|---|---|---|
| Adjuvant | IgG | IgG1 | IgG2a | IgG | IgG1 | IgG2a |
| Non | 4,146 | 531 | 293 | 157,203 | 4,467 | 9,782 |
| MPL ™ | 3,381 | 171 | 318 | 431,529 | 23,465 | 20,422 |
| MPL ™ + GM-CSF | 7,895 | 50 | 980 | 790,193 | 2,478 | 82,690 |
| MPL ™ SE | 135,016 | 297 | 13,339 | 3,945,614 | 10,805 | 342,322 |
| MPL ™ SE + | 106,008 | 725 | 8,772 | 3,304,231 | 31,920 | 201,787 |

Individual week 6 IgG titer geometric means against the recombinant Porin B protein were also determined. The results are given in Table 26.

TABLE 26

Individual IgG Titers

| Adjuvant | Geometric Mean | Standard Error |
|---|---|---|
| None | 100,089 | 63,467 |
| MPL ™ | 217,114 | 451,611 |
| MPL ™ + GM-CSF | 649,801 | 353,863 |
| MPL ™ SE | 1,917,908 | 1,478,357 |
| MPL ™ SE + GM-CSF | 2,144,567 | 858,184 |

Experiment 11

Immunization of Swiss-Webster Mice with a *Neisseria gonorrhoeae* Porin B Protein and Various Adjuvants Outbred Swiss-Webster mice were divided into six groups of five mice each. Each group received 1 µg of recombinant Porin B protein (from strain FA1090 with 16 amino acids at the amino-terminus from a phage, followed by the mature form of the Porin B protein). The first group did not receive an adjuvant (protein was formulated in PBS); the second group received 40 ng of IL-12; the third group received 50 µg of MPL™; the fourth group received MPL™ plus 40 ng IL-12; the fifth group received 25 µg MPL™ SE; the sixth group MPL™ SE plus 40 ng IL-12. Mice were immunized subcutaneously in the rump with a total volume of 0.2 ml. Immunizations were administered at week 0 and week 4.

Example 26

Reciprocal Anti-Porin B Protein IgG Endpoint Subclass Titers and Vaginal Lavage IgG and IgA Titers Mice were bled the day prior to each immunization, and at 13 days after the final immunization. Serum was analyzed from pools from mice within groups. Reciprocal endpoint anti-Porin B protein IgG subclass titers were measured from pooled serum (n=5 Swiss-Webster) by vaginal lavage, and IgG and IgA vaginal wash titers were measured, each at week 3 and at week 6. The results are given in Table 27. All day 0 pre-immunization titers were less than 50. The starting dilution for vaginal lavage analysis was 1/5.

TABLE 27

Reciprocal anti-Porin B Protein IgG Endpoint Sublass Titers and Vaginal Lavage IgG and IgA Titers

| Adjuvant | Week 3 | | | Week 6 | | | Vaginal Wash | |
|---|---|---|---|---|---|---|---|---|
| | IgG | IgG1 | IgG2a | IgG | IgG1 | IgG2a | IgG | IgA |
| None | 9,084 | 1,872 | 2,872 | 408,944 | 9,314 | 64,500 | 80 | 5 |
| IL-12 | 7,266 | 2,578 | 2,071 | 571,325 | 6,278 | 58,552 | 93 | 5 |
| MPL ™ | 5,656 | 500 | 1,925 | 265,127 | 76,640 | 60,910 | 54 | 5 |
| MPL ™ + IL-12 | 28,274 | 1,442 | 11,348 | 3,747,987 | 120,112 | 44,997 | 88 | 5 |
| MPL ™ SE | 53,056 | 8,543 | 17,550 | 5,133,154 | 513,236 | 622,514 | 338 | 5 |
| MPL ™ SE + IL-12 | 757,133 | 5,622 | 33,259 | 10,935,000 | 210,478 | 471,552 | 3,036 | 5 |

Experiment 12

Immunization of Balb/c Mice with Respiratory Syncytial Virus F Protein and Various Adjuvants Balb/c mice were divided into seven groups of five mice each. Each group received 3 µg of purified native Human Respiratory syncytial virus (RSV) F protein (in the dimeric form). The first group did not receive an adjuvant (protein was formulated in PBS); the second group received 100 µg of aluminum phosphate (alum); the third group received 20 µg of Stimulon™ QS-21 (Aquila Biopharmaceuticals, Inc., Framingham, Mass.); the fourth group received 50 µg MPL™; the fifth group received MPL™ plus 5 µg GM-CSF; the sixth group received 25 µg MPL™ SE; the seventh group received MPL™ SE plus 5 µg GM-CSF. Mice were immunized intramuscularly with a total volume of 0.2 ml in the upper thigh. Immunizations were administered at week 0 and week 4.

Example 27

Reciprocal Anti-RSV F Protein IgG Endpoint Subclass Titers

Mice were bled the day prior to each immunization, and at 13 days after the final immunization. Serum was analyzed from pools from mice within groups. Reciprocal endpoint anti-RSV F protein IgG subclass titers were measured from pooled serum (n=5 Balb/c). The results are given in Table 28. All day 0 pre-immunization titers were less than 50.

Example 28

Spleen Cell Proliferation

Spleen cell proliferation in response to in vitro stimulation with 2.5 µg/ml RSV F protein and various adjuvant formulations (the same as in Example 27) was measured. Spleen cells were harvested at 14 days post-secondary immunization and were established in culture at a density of $5 \times 10^5$ cells. Cells were cultured for a total of 96 hours. $^3$H-thymidine was added to cultures for the last 18 hours. Data are presented as a proliferation index normalized to cells stimulated in culture with ConA ([mean cpm Antigen/mean cpm ConA]−[mean cpm medium/mean cpm ConA])×100. As a result, cells cultured in medium have a background proliferation of 0. The results are given in Table 29.

TABLE 29

| Spleen cell proliferation | |
|---|---|
| Adjuvant | Normalized Proliferation Index |
| None | 18.1 |
| Alum | 13.1 |
| Stimulon ™ QS-21 | 0.8 |
| MPL ™ | 0.4 |
| MPL ™ + GM-CSF | 20.0 |
| MPL ™ SE | 17.8 |
| MPL ™ + SE GM-CSF | 16.3 |

TABLE 28

Reciprocal anti-RSV F Protein IgG Endpoint Sublass Titers

| Adjuvant | Week 3 | | | Week 6 | | |
|---|---|---|---|---|---|---|
| | IgG | IgG1 | IgG2a | IgG | IgG1 | IgG2a |
| None | 18,452 | 3,698 | 319 | 539,156 | 3,119,905 | 80,855 |
| Alum | 66,710 | 35,839 | 4,321 | 5,417,001 | 3,226,833 | 291,474 |
| Stimulon ™ QS-21 | 313,665 | 150,988 | 176,080 | 12,113,156 | 2,902,521 | 4,324,004 |
| MPL ™ | 124,197 | 28,134 | 11,882 | 3,310,838 | 900,863 | 1,057,108 |
| MPL ™ + GM-CSF | 419,873 | 91,649 | 65,453 | 10,343,803 | 753,890 | 688,554 |
| MPL ™ SE | 374,992 | 44,115 | 147,366 | 19,333,189 | 1,493,284 | 6,314,264 |
| MPL ™ SE + GM-CSF | 1,748,272 | 51,966 | 267,256 | 30,816,193 | 1,716,850 | 2,641,258 |

Experiment 13

Immunization of Balb/c Mice with Respiratory Syncytial Virus F Protein and Various Adjuvants The protocol of Experiment 12 was repeated (immunizations at week 0 and week 4 with RSV F protein with or without various adjuvants).

Example 29

Reciprocal Anti-RSV F Protein IgG Endpoint Subclass Titers

Mice were bled the day prior to each immunization, and at 13 days after the final immunization. Serum was analyzed from pools from mice within groups. Reciprocal endpoint anti-RSV F protein IgG subclass titers were measured from pooled serum (n=5 Balb/c). The results are given in Table 30. All day 0 pre-immunization titers were less than 50.

TABLE 30

Reciprocal anti-RSV F Protein IgG Endpoint Sublass Titers

| Adjuvant | Week 3 | | | Week 6 | | |
|---|---|---|---|---|---|---|
| | IgG | IgG1 | IgG2a | IgG | IgG1 | IgG2a |
| None | 6,442 | 2,808 | 713 | 5,195,059 | 963,203 | 38,791 |
| Alum | 128,695 | 36,841 | 1,975 | 4,285,993 | 567,972 | 27,668 |
| Stimulon ™ QS-21 | 528,036 | 296,292 | 176,703 | 37,221,721 | 1,823,402 | 1,724,319 |
| MOL ™ | 104,702 | 21,930 | 61,253 | 6,153,833 | 1,384,927 | 955,685 |
| MPL ™ + GM-CSF | 262,128 | 79,888 | 55,249 | 21,054,796 | 3,412,710 | 2,070,305 |
| MPL ™ SE | 184,246 | 47,194 | 180,932 | 31,731,335 | 4,376,601 | 6,406,591 |
| MPL ™ SE + CSF | 375,575 | 70,422 | 289,542 | 27,079,086 | 2,124,043 | 6,341,497 |

Example 30

Spleen Cell CTL Activity

Spleen cell CTL (cytotoxic T-lymphocyte) activity as a consequence of immunization with RSV F protein and the indicated adjuvants was assessed two weeks after the final immunization. Data represent the percent specific CTL activity of spleen cells cultured with RSV-infected target cells at an effector to target cell ratio of 33:1. Percent specific CTL activity was determined as in Example 24, subtracting the CTL activity against non-infected targets from that of activity specific for RSV-infected target cells. Naïve spleen cells were infected with RSV at an MOI (multiplicity of infection) of 1.5 for two hours as a source of in vitro stimulator cells. Responder cells from the spleens of immunized mice were added to simulator cells at a ratio of 5:1, and cultured for six days. On day 5, target cells (Balb/C MHC-H-2d cell line) were infected with RSV at an MOI of 10 for two hours and incubated overnight. On day 6, infected and non-infected target cells were harvested and pulsed with $^{51}$Cr. In vitro effector cells were then added to target cells at an E:T ratio ranging from 100:1 to 3:1. Chromium release was measured after four hours of incubation. The results are given in Table 31.

TABLE 31

Spleen cell CTL activity

| Adjuvant | Percent CTL Activity |
|---|---|
| None | 1 |
| Alum | 4 |
| Stimulon ™ QS-21 | 53 |
| MPL ™ | 6 |
| MPL ™ + GM-CSF | 15 |
| MPL ™ SE | 30 |
| MPL ™ + SE GM-CSF | 36 |

Experiment 14

Immunization of Balb/c Mice with Respiratory Syncytial Virus F Protein and Various Adjuvants Balb/c mice were divided into six groups of five mice each. Each group received 3 µg of purified native RSV F protein (in the dimeric form). The first group did not receive an adjuvant (protein was formulated in PBS); the second group received 40 ng IL-12; the third group received 50 µg MPL™; the fourth group received MPL™ plus 40 ng IL-12; the fifth group received 25 µg MPL™ SE; the sixth group received MPL™ SE plus 40 ng IL-12. Mice were immunized subcutaneously with a total volume of 0.2 ml in the rump, divided equally between two does given on either side of the tail. Immunizations were administered at week 0 and week 4.

Example 31

Reciprocal Anti-RSV F Protein IgG Endpoint Subclass Titers

Mice were bled the day prior to each immunization, and at 13 days after the final immunization. Serum was analyzed from pools from mice within groups. Reciprocal endpoint anti-RSV F protein IgG subclass titers were measured from pooled serum (n=5 Balb/c). The results are given in Table 32. All day 0 pre-immunization titers were less than 50.

TABLE 32

Reciprocal anti-RSV F Protein IgG Endpoint Sublass Titers

| Adjuvant | Week 3 | | | Week 6 | | |
|---|---|---|---|---|---|---|
| | IgG | IgG1 | IgG2a | IgG | IgG1 | IgG2a |
| Non | 5,332 | 12,925 | 500 | 2,381,899 | 977,782 | 76,226 |
| IL-12 | 13,557 | 3,442 | 500 | 4,459,059 | 1,345,099 | 65,951 |
| MPL ™ | 26,179 | 55,767 | 8,397 | 3,467,097 | 402,128 | 170,252 |
| MPL ™ + IL-12 | 186,516 | 22,321 | 10,800 | 1,546,443 | 420,322 | 253,465 |
| MPL ™ SE | 1,708,358 | 53,608 | 144,876 | 9,075,480 | 565,403 | 1,000,459 |
| MPL ™ SE + IL-12 | 329,050 | 15,788 | 69,794 | 10,935,000 | 386,639 | 1,284,274 |

Example 32

Spleen Cell CTL Activity

Spleen cell CTL activity as a consequence of immunization with RSV F protein and the indicated adjuvants was assessed two weeks after the final immunization. Data represent the percent specific CTL activity of spleen cells cultured with RSV-infected target cells at an effector to target cell ratio of 33:1. Percent specific CTL activity was determined as in Example 24, subtracting the CTL activity against non-infected targets from that of activity specific for RSV-infected target cells. Naïve spleen cells were infected with RSV at an MOI of 1.5 for two hours as a source of in vitro stimulator cells. Responder cells from the spleens of immunized mice were added to simulator cells at a ratio of 5:1, and cultured for six days. On day 5, target cells (Balb/C MHC-H-2d cell line) were infected with RSV at an MOI of 10 for two hours and incubated overnight. On day 6, infected and non-infected target cells were harvested and pulsed with $^{51}$Cr. In vitro effector cells were then added to target cells at an E:T ratio ranging from 100:1 to 3:1. Chromium release was measured after four hours of incubation. The results are given in Table 33.

TABLE 33

Spleen cell CTL activity

| Adjuvant | Percent CTL Activity |
|---|---|
| None | 6 |
| IL-12 | 22 |
| MPL ™ | 15 |
| MPL ™ + IL-12 | 13 |
| MPL ™ SE | 33 |
| MPL ™ + SE IL-12 | 28 |

Experiment 15

Immunization of Balb/c Mice with the Influenza Virus Nucleocapsid Protein and Various Adjuvants Balb/c mice were divided into six groups of five mice each. Each group received 1 µg of the Influenza virus NP (nucleocapsid) protein from the A/dorn/307/72 strain. [check groups] The first group did not receive an adjuvant (peptide was formulated in PBS); the second group received 100 µg of aluminum phosphate (alum); the third group received 50 µg of MPL™; the fourth group received MPL™ plus 5 µg GM-CSF; the fifth group received 25 µg MPL™ SE; the sixth group received MPL™ SE plus 5 µg GM-CSF. Mice were immunized subcutaneously in the rump with a total volume of 0.2 ml. Immunizations were administered at week 0 and week 4.

Example 33

Spleen Cell CTL Activity

Spleen cell CTL activity as a consequence of immunization with the influenza NP peptide and the indicated adjuvants was assessed two weeks after the final immunization. The assessment was carried out following the procedure of Example 32 using peptide-pulsed target p815 cells (the peptide corresponded to amino acids 147-155 of NP and had the sequence: Thr Tyr Gln Arg Thr Arg Ala Leu Val (SEQ ID NO:14). The inclusion of GM-CSF in the formulations containing MPL™ or MPL™ SE resulted in a marked reduction of CTL activity (data not shown).

BIBLIOGRAPHY

1. Mosmann, T. R., et al., *J. Immunol.*, 136, 2348-2357 (1986).
2. U.S. Pat. No. 4,912,094.
3. Ahlers, J. D., et al., *J. Immunol.*, 158, 3947-3958 (1997).
4. Scharton-Kersten, T., et al., *J. Immunol.* 154, 5320-5330 (1995).
5. Ghalib, H. W., et al., *J. Immunol.*, 154, 4623-4629 (1995).
6. Murray, H. W., and Hariprashad, J., *J. Exp. Med.*, 181, 387-391 (1995).
7. U.S. Pat. No. 5,571,515.
8. Finkelman, F. D., and Holmes, J., *Ann. Rev. Immunol.*, 8, 303-333 (1990).
9. Snapper, C. M., et al., *J. Exp. Med.*, 175, 1367-1371 (1992).
10. Kobayashi, M., et al., *J. Exp. Med.*, 170, 827-845 (1989).
11. Published International Patent Application Number WO 90/05147.
12. U.S. Pat. No. 5,078,996.
13. U.S. Pat. No. 5,229,496.
14. U.S. Pat. No. 5,073,627.
15. Alderson, M. R., et al., *J. Exp. Med.*, 178, 669-674 (1993).
16. Snapper, C. M., et al., *J. Immunol.*, 154, 5842-5850 (1995).
17. U.S. Pat. No. 5,013,548.
18. U.S. Pat. No. 5,019,387.
19. Charbit, A., et al., *Vaccine*, 11, 1221-1228 (1993).
20. Natuk, R. J., et al., *AIDS Res. Hum. Retroviruses*, 9, 395-404 (1993).
21. Johnson, R. P., et al., *J. Virol.*, 68, 3145-3153 (1994).
22. Fuller, D. H., et al., *AIDS Res. Hum. Retroviruses*, 10, 1433-1441 (1994).
23. Berzofsky, J. A., et al., *J. Clin. Invest.*, 88, 876-884 (1991).
24. Palker, T. J., et al., *J. Immunol.*, 142, 3612-3619 (1989).
25. Hart, M. K., et al., *J. Immunol.*, 145, 2677-2685 (1990).
26. Haynes, B. F., et al., *J. Immunol.*, 151, 1646-1653 (1993).

27. Hart, M. K., et al., *Proc. Natl. Acad. Sci., USA*, 88, 9448-9452 (1991).
28. Bartlett, J. A., et al., *AIDS*, 12, 1291-1300 (1998).
29. Haynes, B. F., et al., *AIDS Res. Hum. Retroviruses*, 11, 211-221 (1998).
30. U.S. Pat. No. 5,861,243.
31. U.S. Pat. No. 5,932,218.
32. U.S. Pat. No. 5,939,074.
33. U.S. Pat. No. 5,993,819.
34. U.S. Pat. No. 6,037,135.
35. Published European Patent Application Number 671,947.
36. Staats, H. F., et al., *J. Immunol.*, 157, 462-472 (1996).
37. Porgador, A., et al., *J. Immunol.*, 158, 834-841 (1997).
38. Allen, T. M., et al., *J. Immunol.*, 160, 6062-6071 (1998).
39. Miller, M. D., et al., *J. Immunol.*, 147, 320-329 (1991).
40. Egan, M. A., et al., *J. Virol.*, 73, 5466 (1999).
41. Hart, M. K., *J. Immunol.*, 145, 2677-2685 (1990).
42. U.S. Pat. No. 5,736,361.
43. U.S. Pat. No. 5,223,254.
44. Published International Patent Application Number WO 98/20734.
45. U.S. Pat. No. 5,830,877.
46. Published International Patent Application Number WO 99/51259.
47. Published International Patent Application Number WO 99/27944.
48. U.S. Pat. No. 4,666,829.
49. U.S. Pat. No. 5,593,972.
50. Kuroda, M. J., et al., *J. Exp. Med.*, 187, 1373-1381 (1998).

What is claimed is:

1. An antigenic composition consisting of an antigen and an effective adjuvanting amount of the combination of: (1) 3-O-deacylated monophosphoryl lipid A or monophosphoryl lipid A, and (2) granulocyte macrophage colony stimulating factor (GM-CSF), together with a diluent or carrier.

2. The antigenic composition of claim 1, where the antigen is a polypeptide, peptide or fragment derived from a protein.

3. The antigenic composition of claim 1, where 3-O-deacylated monophosphoryl lipid A is used in the form of a stable oil-in-water emulsion.

4. The antigenic composition of claim 1, where the antigen is derived from a pathogenic virus.

5. The antigenic composition of claim 1, where the antigen is derived from a pathogenic bacterium.

6. The antigenic composition of claim 1, where the antigen is derived from a pathogenic fungus.

7. The antigenic composition of claim 1, where the antigen is derived from a pathogenic parasite.

8. The antigenic composition of claim 1, where the antigen is derived from a cancer cell or tumor cell.

9. The antigenic composition of claim 1, where the antigen is derived from an allergen.

10. The antigenic composition of claim 1, where the antigen is derived from AP protein or peptide thereof, or an antibody thereto.

11. A method for increasing the ability of an antigenic composition containing an antigen from a pathogenic virus to elicit an immune response in a vertebrate host against said pathogenic virus, which comprises administering to said host an antigenic composition of claim 4.

12. A method for increasing the ability of an antigenic composition containing an antigen from a pathogenic bacterium to elicit the immune response of a vertebrate host, which comprises administering to said host an antigenic composition of claim 5.

13. A method for increasing the ability of an antigenic composition containing an antigen from a pathogenic fungus to elicit the immune response of a vertebrate host, which comprises administering to said host an antigenic composition of claim 6.

14. A method for increasing the ability of an antigenic composition containing an antigen from a pathogenic parasite to elicit the immune response of a vertebrate host, which comprises administering to said host an antigenic composition of claim 7.

15. A method for increasing the ability of an antigenic composition containing an antigen from a pathogenic virus to elicit cytotoxic T lymphocytes responses in a vertebrate host, which comprises administering to said host an antigenic composition of claim 4.

16. A method for increasing the ability of an antigenic composition containing an antigen from a pathogenic bacterium to elicit cytotoxic T lymphocytes in a vertebrate host, which comprises administering to said host an antigenic composition of claim 5.

17. A method for increasing the ability of an antigenic composition containing an antigen from a pathogenic fungus to elicit cytotoxic T lymphocytes in a vertebrate host, which comprises administering to said host an antigenic composition of claim 6.

18. A method for increasing the ability of an antigenic composition containing an antigen from a pathogenic parasite to elicit cytotoxic T lymphocytes in a vertebrate host, which comprises administering to said host an antigenic composition of claim 7.

19. A method for increasing the ability of an antigenic composition containing a selected cancer antigen or tumor-associated antigen from a cancer cell or tumor cell to elicit a therapeutic or prophylactic anti-cancer effect in a vertebrate host, which comprises administering to said host an antigenic composition of claim 8.

20. A method for increasing the ability of an antigenic composition containing a selected allergen to moderate an allergic response in a vertebrate host, which comprises administering to said host an antigenic composition of claim 9.

21. A method for increasing the ability of an antigenic composition to prevent or treat disease characterized by amyloid deposition in a vertebrate host, which comprises administering to said host an antigenic composition of claim 10.

22. The antigenic composition of claim 4, where the antigen is from human immunodeficiency virus (HIV).

23. The antigenic composition of claim 22, where the HIV antigen is an HIV protein, polypeptide, peptide or fragment derived from said protein.

24. The antigenic composition of claim 23 where the antigen is the HIV peptide having the amino acid sequence: Lys Gln Ile Ile Asn Met Trp Gln Glu Val Gly Lys Ala Met Tyr Ala Cys Thr Arg Pro Asn Tyr Asn Lys Arg Lys Arg Ile His Ile Gly Pro Gly Arg Ala Phe Tyr Thr Thr Lys (SEQ ID NO:1), or Lys Gln Ile Ile Asn Met Trp Gln Glu Val Gly Lys Ala Met Tyr Ala Cys Thr Arg Pro Asn Tyr Asn Lys Arg Lys Arg Ile His Ile Gly Pro Gly Arg Ala Phe Tyr Thr Thr Lys (SEQ ID NO:2).

25. The antigenic composition of claim 22, where 3-O-deacylated monophosphoryl lipid A is used in the form of a stable oil-in-water emulsion.

26. The antigenic composition of claim 4, where the antigen is from simian immunodeficiency virus (SIV).

27. The antigenic composition of claim 26, where the SIV antigen is an SIV protein, polypeptide, peptide or fragment derived from said protein.

28. The antigenic composition of claim 27, where the SIV peptide selected from the peptides consisting of the amino acid sequences: Cys Thr Pro Tyr Asp Ile Asn Gln Met (SEQ ID NO:3), Ser Thr Pro Pro Leu Val Arg Leu Val (SEQ ID NO:4), Tyr Ala Pro Pro Ile Ser Gly Gln Ile (SEQ ID NO:5), Glu Leu Tyr Lys Tyr Lys Val Val Lys Ile Glu Pro Leu Gly Val Ala Pro Thr Lys Ala Cys Thr Pro Tyr Asp Ile Asn Gln Met (SEQ ID NO:7), Glu Leu Tyr Lys Tyr Lys Val Val Lys Ile Glu Pro Leu Gly Val Ala Pro Thr Lys Ala Ser Thr Pro Pro Leu Val Arg Leu Val (SEQ ID NO:8) and Glu Leu Tyr Lys Tyr Lys Val Val Lys Ile Glu Pro Leu Gly Val Ala Pro Thr Lys Ala Tyr Ala Pro Pro Ile Ser Gly Gln Ile (SEQ ID NO:9).

29. The antigenic composition of claim 26, where 3-O-deacylated monophosphoryl lipid A is used in the form of a stable oil-in-water emulsion.

30. The antigenic composition of claim 5, where the antigen is from *Neisseria gonorrhoeae*.

31. The antigenic composition of claim 30, where the *Neisseria gonorrhoeae* antigen is a *Neisseria gonorrhoeae* protein, polypeptide, peptide or fragment derived from said protein.

32. The antigenic composition of claim 31, where the antigen is the *Neisseria gonorrhoeae* Porin B protein.

33. The antigenic composition of claim 30, where 3-O-deacylated monophosphoryl lipid A is used in the form of a stable oil-in-water emulsion.

34. The antigenic composition of claim 4, where the antigen is from human Respiratory syncytial virus (RSV).

35. The antigenic composition of claim 34, where the RSV antigen is an RSV protein, polypeptide, peptide or fragment derived from said protein.

36. The antigenic composition of claim 35, where the antigen is the RSV fusion (F) protein.

37. The antigenic composition of claim 34, where 3-O-deacylated monophosphoryl lipid A is used in the form of a stable oil-in-water emulsion.

38. A method for increasing the ability of an antigenic composition containing an HIV antigen to elicit an immune response to said antigen in a vertebrate host, which comprises administering to said host an antigenic composition of claim 22.

39. The method of claim 38, where the HIV antigen is the HIV peptide having the amino acid sequence: Lys Gln Ile Ile Asn Met Trp Gln Glu Val Gly Lys Ala Met Tyr Ala Cys Thr Arg Pro Asn Tyr Asn Lys Arg Lys Arg Ile His Ile Gly Pro Gly Arg Ala Phe Tyr Thr Thr Lys (SEQ ID NO:1).

40. The method of claim 38, where the HIV antigen is the HIV peptide having the amino acid sequence: Lys Gln Ile Ile Asn Met Trp Gln Glu Val Gly Lys Ala Met Tyr Ala Thr Arg Pro Asn Tyr Asn Lys Arg Lys Arg Ile His Ile Gly Pro Gly Arg Ala Phe Tyr Thr Thr Lys (SEQ ID NO:2).

41. A method for increasing the ability of an antigenic composition containing an HIV antigen to elicit cytotoxic T lymphocyte responses in a vertebrate host, which comprises administering to said host an antigenic composition of claim 22.

42. The method of claim 41, where the HIV antigen is the HIV peptide having the amino acid sequence: Lys Gln Ile Ile Asn Met Trp Gln Glu Val Gly Lys Ala Met Tyr Ala Cys Thr Arg Pro Asn Tyr Asn Lys Arg Lys Arg Ile His Ile Gly Pro Gly Arg Ala Phe Tyr Thr Thr Lys (SEQ ID NO:1).

43. The method of claim 41, where the HIV antigen is the HIV peptide having the amino acid sequence: Lys Gln Ile Ile Asn Met Trp Gln Glu Val Gly Lys Ala Met Tyr Ala Thr Arg Pro Asn Tyr Asn Lys Arg Lys Arg Ile His Ile Gly Pro Gly Arg Ala Phe Tyr Thr Thr Lys (SEQ ID NO:2).

44. A method for increasing the ability of an antigenic composition containing an SIV antigen to elicit the immune response of a vertebrate host, which comprises administering to said host an antigenic composition of claim 26.

45. The method of claim 44, where the SIV antigen is an SIV peptide selected from the peptides consisting of the amino acid sequences: Cys Thr Pro Tyr Asp Ile Asn Gln Met (SEQ ID NO:3), Ser Thr Pro Pro Leu Val Arg Leu Val (SEQ ID NO:4), Tyr Ala Pro Pro Ile Ser Gly Gln Ile (SEQ ID NO:5), Glu Leu Tyr Lys Tyr Lys Val Val Lys Ile Glu Pro Leu Gly Val Ala Pro Thr Lys Ala Cys Thr Pro Tyr Asp Ile Asn Gln Met (SEQ ID NO:7), Glu Leu Tyr Lys Tyr Lys Val Val Lys Ile Glu Pro Leu Gly Val Ala Pro Thr Lys Ala Ser Thr Pro Pro Leu Val Arg Leu Val (SEQ ID NO:8) and Glu Leu Tyr Lys Tyr Lys Val Val Lys Ile Glu Pro Leu Gly Val Ala Pro Thr Lys Ala Tyr Ala Pro Pro Ile Ser Gly Gln Ile (SEQ ID NO:9).

46. A method for increasing the ability of an antigenic composition containing an SIV antigen to elicit cytotoxic T lymphocytes in a vertebrate host, which comprises administering to said host an antigenic composition of claim 26.

47. The method of claim 46, where the SIV antigen is an SIV peptide selected from the peptides consisting of the amino acid sequences: Cys Thr Pro Tyr Asp Ile Asn Gln Met (SEQ ID NO:3), Ser Thr Pro Pro Leu Val Arg Leu Val (SEQ ID NO:4), Tyr Ala Pro Pro Ile Ser Gly Gln Ile (SEQ ID NO:5), Glu Leu Tyr Lys Tyr Lys Val Val Lys Ile Glu Pro Leu Gly Val Ala Pro Thr Lys Ala Cys Thr Pro Tyr Asp Ile Asn Gln Met (SEQ ID NO:7), Glu Leu Tyr Lys Tyr Lys Val Val Lys Ile Glu Pro Leu Gly Val Ala Pro Thr Lys Ala Ser Thr Pro Pro Leu Val Arg Leu Val (SEQ ID NO:8) and Glu Leu Tyr Lys Tyr Lys Val Val Lys Ile Glu Pro Leu Gly Val Ala Pro Thr Lys Ala Tyr Ala Pro Pro Ile Ser Gly Gln Ile (SEQ ID NO:9).

48. A method for increasing the ability of an antigenic composition containing a *Neisseria gonorrhoeae* antigen to elicit the immune response of a vertebrate host, which comprises administering to said host an antigenic composition of claim 30.

49. The method of claim 48, where the *Neisseria gonorrhoeae* antigen is the *Neisseria gonorrhoeae* Porin B protein.

50. A method for increasing the ability of an antigenic composition containing a *Neisseria gonorrhoeae* antigen to elicit cytotoxic T lymphocytes in a vertebrate host, which comprises administering to said host an antigenic composition of claim 30.

51. The method of claim 50, where the *Neisseria gonorrhoeae* antigen is the *Neisseria gonorrhoeae* Porin B protein.

52. A method for increasing the ability of an antigenic composition containing a human Respiratory syncytial virus (RSV) antigen to elicit the immune response of a vertebrate host, which comprises administering to said host an antigenic composition of claim 34.

53. The method of claim 52, where the RSV antigen is the RSV fusion (F) protein.

54. A method for increasing the ability of an antigenic composition containing an RSV antigen to elicit cytotoxic T lymphocytes in a vertebrate host, which comprises administering to said host an antigenic composition of claim 34.

55. The method of claim 54, where the RSV antigen is the RSV fusion (F) protein.

\* \* \* \* \*

UNITED STATES PATENT AND TRADEMARK OFFICE
CERTIFICATE OF CORRECTION

PATENT NO. : 7,611,721 B1  Page 1 of 1
APPLICATION NO. : 10/009473
DATED : November 3, 2009
INVENTOR(S) : Michael Hagen It is certified that error appears in the above-identified patent and that said Letters Patent is hereby corrected as shown below:

Title page left column
add
Related U.S. Application Data
Item (60) Provisional application No. 60/133,963, filed on May 13, 1999.

Signed and Sealed this

Twenty-third Day of February, 2010

David J. Kappos
*Director of the United States Patent and Trademark Office*